(12) United States Patent
Douglas et al.

(10) Patent No.: US 11,574,435 B1
(45) Date of Patent: Feb. 7, 2023

(54) MULTI-USER EXTENDED REALITY VIEWING TECHNIQUE

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

(*) Notice: Subject to any disclaimer, the term of this patent is extended or adjusted under 35 U.S.C. 154(b) by 0 days.

(21) Appl. No.: 17/079,479

(22) Filed: Oct. 25, 2020

Related U.S. Application Data

(63) Continuation-in-part of application No. 17/072,350, filed on Oct. 16, 2020, now Pat. No. 11,003,948, and a continuation-in-part of application No. 17/033,892, filed on Sep. 27, 2020, now Pat. No. 10,964,095, and a continuation-in-part of application No. 16/927,886, filed on Jul. 13, 2020, now Pat. No. 11,475,625, and a continuation-in-part of application No. 16/842,631, filed on Apr. 7, 2020, now Pat. No. 11,003,342.

(51) Int. Cl.
*G06T 15/20* (2011.01)
*G06F 3/01* (2006.01)
*G06F 3/14* (2006.01)

(52) U.S. Cl.
CPC .............. *G06T 15/20* (2013.01); *G06F 3/013* (2013.01); *G06F 3/1454* (2013.01)

(58) Field of Classification Search
CPC ........ G06F 3/011; G06F 3/016; G06F 3/0304; G06T 19/20
See application file for complete search history.

(56) References Cited

U.S. PATENT DOCUMENTS

2018/0197624 A1* 7/2018 Robaina .............. G06F 16/2379
2019/0228582 A1* 7/2019 Yerkes .................... G06T 13/20

OTHER PUBLICATIONS

Gil; https://gilscvblog.com/2013/10/04/a-tutorial-on-binary-descriptors-part-3-the-orb-descriptor/; 2013. (Year: 2013).*
Mandalika, V., Chernoglazov, A. I., Billinghurst, M., Bartneck, C., Hurrell, M. A., Ruiter, N., Butler, A., & Butler, P. H. (2018). A Hybrid 2D/3D User Interface for Radiological Diagnosis. Journal of digital imaging, 31(1), 56-73. https://doi.org/10.1007/s10278-017-0002-6 (Year: 2018).*
Elsayed M, Kadom N, Ghobadi C, et al. Virtual and augmented reality: potential applications in radiology. Acta Radiologica. Jan. 13, 2020;61(9):1258-1265. doi:10.1177/0284185119897362 (Year: 2020).*

\* cited by examiner

*Primary Examiner* — Ross Varndell

(57) ABSTRACT

In this patent, an improved multi-user extended reality viewing technique is disclosed. A first user and a second user can be geographically separated and view the same volume. The first user can manipulate a virtual object and the second user can see the manipulated virtual object. A set of techniques are disclosed herein to cause the virtual object as it is presented to each user to be eye appealing and prevent dizziness and nausea.

20 Claims, 20 Drawing Sheets

GENERATING AN OPTIMIZED VIEW FOR A SECOND USER WHEN FIRST USER ROTATES THE VIRTUAL OBJECT

User 1 at t = 1

User 2 at t = 1

User 1 at t = 2

User 2 at t = 2

GENERATING AN OPTIMIZED VIEW FOR A SECOND USER WHEN FIRST USER CHANGES VIEWPOINT AND VIEWING ANGLE

User 1 at t = 1

302

301

300

User 2 at t = 1

305

304

303

User 1 at t = 2

302

307

306

User 2 at t = 2

308

304

303

GENERATING AN OPTIMIZED VIEW FOR A SECOND USER WHEN FIRST USER CHANGES VIEWING DISTANCE

User 1 at t = 1

User 2 at t = 1

User 1 at t = 2

User 2 at t = 2

A FRIST USER CHANGES VIEWPOINT AND SECOND USER SEES CHANGE IN VIRTUAL OBJECT POSITION

Fig. 5A User 1

| Time point | View point | Object position |
|---|---|---|
| 1 | x = 100<br>y = 100<br>z = 100 | x = 300<br>y = 100<br>z = 100 |
| 2 | x = 110<br>y = 100<br>z = 100 | x = 300<br>y = 100<br>z = 100 |
| 3 | x = 120<br>y = 100<br>z = 100 | x = 300<br>y = 100<br>z = 100 |
| 4 | x = 130<br>y = 100<br>z = 100 | x = 300<br>y = 100<br>z = 100 |
| 5 | x = 140<br>y = 100<br>z = 100 | x = 300<br>y = 100<br>z = 100 |
| 6 | x = 150<br>y = 100<br>z = 100 | x = 300<br>y = 100<br>z = 100 |
| 7 | x = 160<br>y = 100<br>z = 100 | x = 300<br>y = 100<br>z = 100 |
| 8 | x = 170<br>y = 100<br>z = 100 | x = 300<br>y = 100<br>z = 100 |
| 9 | x = 180<br>y = 100<br>z = 100 | x = 300<br>y = 100<br>z = 100 |

Fig. 5B User 2

| Time point | View point | Object position |
|---|---|---|
| 1 | x = 100<br>y = 100<br>z = 100 | x = 300<br>y = 100<br>z = 100 |
| 2 | x = 100<br>y = 100<br>z = 100 | x = 290<br>y = 100<br>z = 100 |
| 3 | x = 100<br>y = 100<br>z = 100 | x = 280<br>y = 100<br>z = 100 |
| 4 | x = 100<br>y = 100<br>z = 100 | x = 270<br>y = 100<br>z = 100 |
| 5 | x = 100<br>y = 100<br>z = 100 | x = 260<br>y = 100<br>z = 100 |
| 6 | x = 100<br>y = 100<br>z = 100 | x = 250<br>y = 100<br>z = 100 |
| 7 | x = 100<br>y = 100<br>z = 100 | x = 240<br>y = 100<br>z = 100 |
| 8 | x = 100<br>y = 100<br>z = 100 | x = 230<br>y = 100<br>z = 100 |
| 9 | x = 100<br>y = 100<br>z = 100 | x = 220<br>y = 100<br>z = 100 |

PREDETERMINED CRITERIA TO DETERMINE FILTER VERSES SHARE

EXTENT OF MOVEMENT
- Head Display Unit Movement
    - Distance cut off (e.g., in cm)
    - Rotation cut off (e.g., in degrees)
- Geo-registered Tool Movement
    - Distance cut off (e.g., in cm)
    - Rotation cut off (e.g., in degrees)
- Digital object (e.g., Virtual tool) Movement
    - Distance cut off (e.g., in cm)
    - Rotation cut off (e.g., in degrees)

RATE OF MOVEMENT
- Head Display Unit Movement
    - Linear movement (e.g., in cm/sec)
    - Rotational movement (e.g., in degrees/sec)
- Geo-registered Tool Movement
    - Linear movement (e.g., in cm/sec)
    - Rotational movement (e.g., in degrees/sec)
- Digital object (e.g., Virtual tool) Movement
    - Linear movement (e.g., in cm/sec)
    - Rotational movement (e.g., in degrees/sec)

IMAGE MANIPULATION OF VIRTUAL OBJECT
- Filtering (e.g., changing number of voxels displayed)
- Brightness adjustment (e.g., lumens/sec)
- Contrast adjustment (e.g., in degrees/sec)
- Visual enhancement features (e.g., lines)

Fig. 7

USING A MEASUREMENT AS A PREDETERMINED CRITERIA

SMOOTHING TECHNIQUES IMPLEMENTED IN GENERATING AN OPTIMIZED VIEW FOR A SECOND USER WITHOUT DELAY
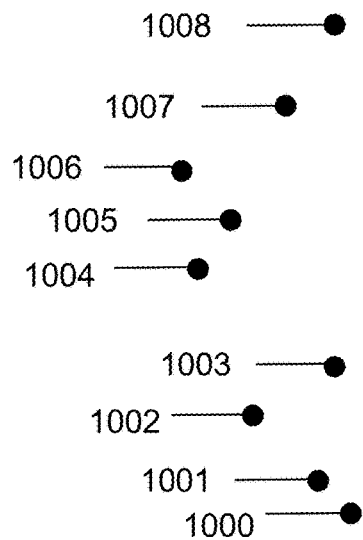
Fig. 10A User 1's viewpoint at 9 time points
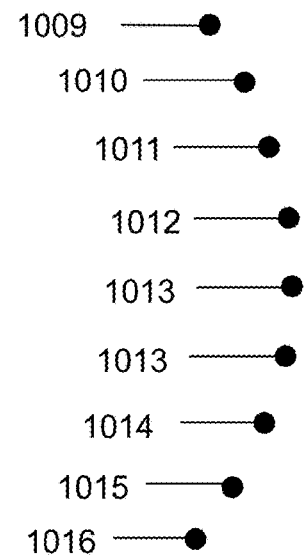
Fig. 10B Virtual object's location as seen by user 2 at 9 time points

SMOOTHING TECHNIQUES IMPLEMENTED IN GENERATING A MIRRORED VIEW FOR A SECOND USER WITH DELAY
Fig. 11A User 1 at
t = 1, 2, 3, 4, 5, 6, 7, 8, 9
Fig. 11B User 2 at
t = 1, 2, 3, 4, 5, 6, 7, 8, 9
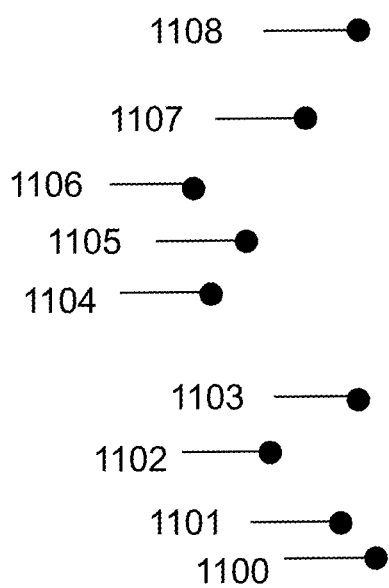
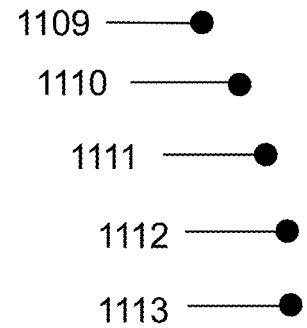

DISPLAY OF A FIRST USER'S ACTIONS ON A SECOND USER'S DISPLAY

Fig. 13A User 1's action of viewing at a first time point

Fig. 13B User 2's view through a HDU at the first time point

Fig. 13C User 1's action of virutal cutting at a second time point

Fig. 13D User 2's view through the HDU at the second time point

Fig. 13E User 1's action of removing the tissue at a third time point

Fig. 13F User 2's view through the HDU at the third time point

INTERACTIVE VIEWING AND MANIPULATION OF A VOLUME

ADVANCED TECHNIQUES TO ENHANCE VIEWING

Additional processing techniques

Advanced volume rendering techniques
- Prioritized volume rendering
- Tandem volume rendering
- Use of a precision sub-volume

Other advanced viewing strategies
- Eye tracking techniques
- Dynamic deformation of a 3D dataset
- Double windowing technique
- Use of virtual tools
- Use of geo-registered tools

Secondary analysis
- Radiologist Assisted Machine Learning
- Smart image consulting process

Fig. 16

ADVANCED OPTION WHEREIN A SECOND USER CAN SEE THE LOCATION WHERE A FIRST USER IS LOOKING

EYE TRACKING TEACHING TECHNIQUES IMPLEMENTED IN GENERATING A SECOND USER VIEW
Fig. 18A User 1 at
t = 1, 2, 3, 4, 5, 6, 7, 8, 9
Fig. 18B User 2 at
t = 1, 2, 3, 4, 5, 6, 7, 8, 9
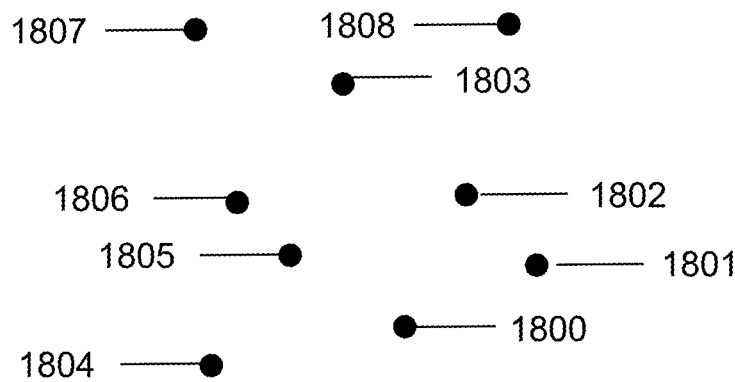
No eye tracking dot shown
Fig. 18C User 1 at
t = 1, 2, 3, 4, 5, 6, 7, 8, 9
Fig. 18D User 2 at
t = 7, 8, 9
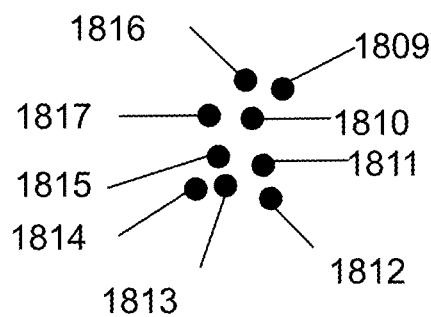
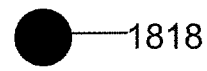

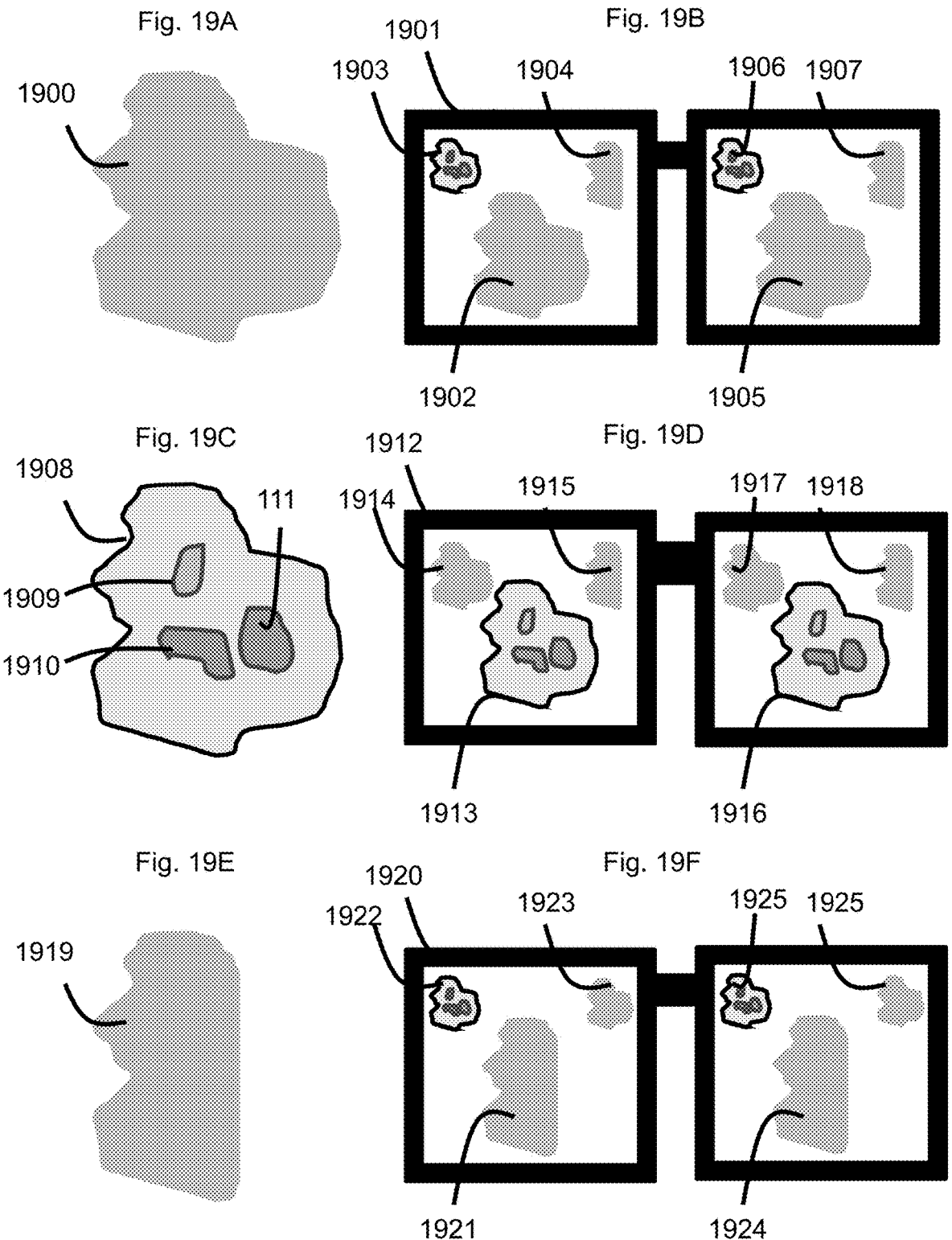

GEOGRAPHICALLY SEPARATED USERS
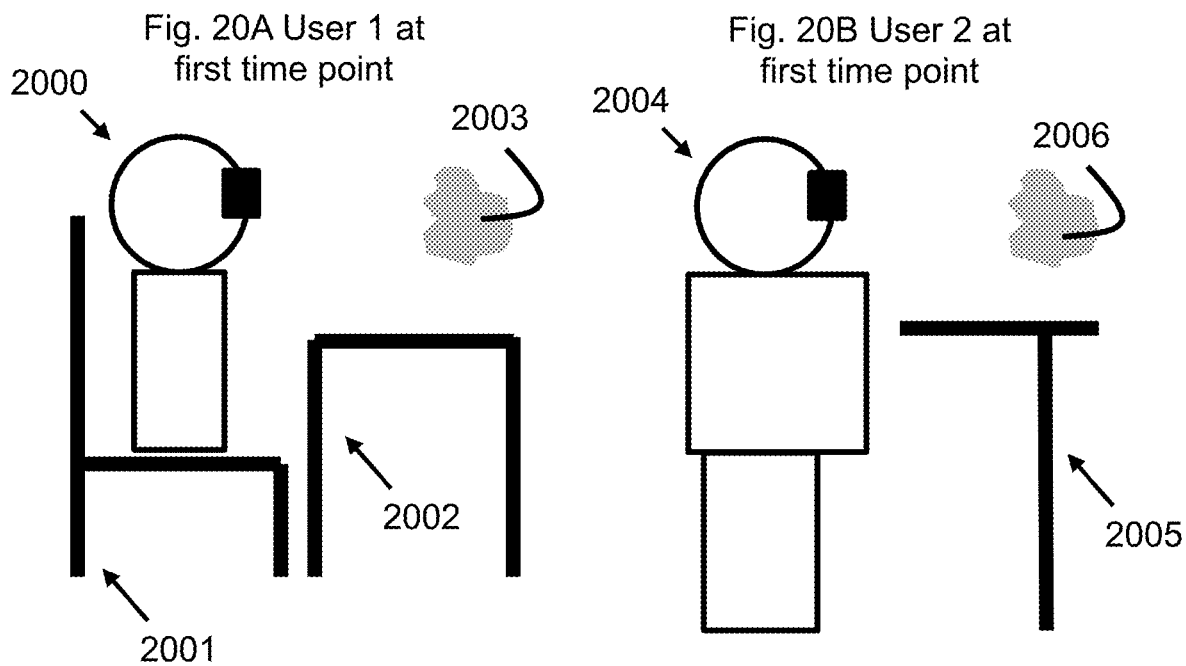
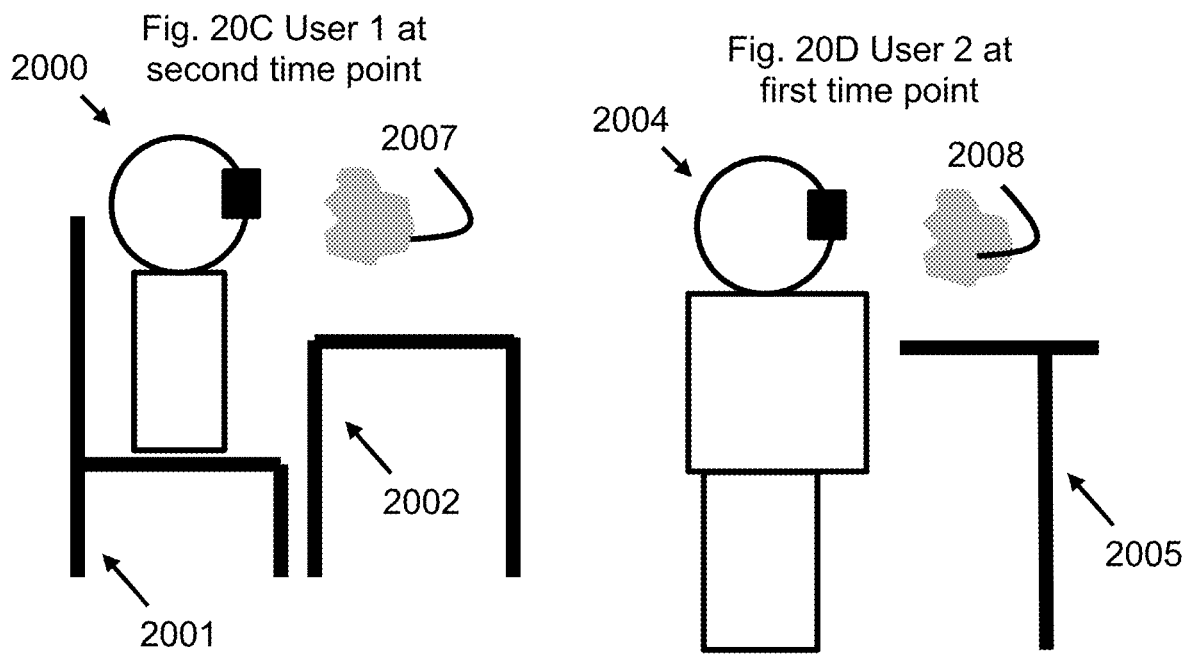

MULTI-USER EXTENDED REALITY VIEWING TECHNIQUE

CROSS REFERENCE TO RELATED APPLICATIONS

This application is a continuation-in-part of U.S. patent application Ser. No. 17/072,350 filed on Oct. 16, 2020, a continuation-in-part of U.S. patent application Ser. No. 17/033,892 filed on Sep. 27, 2020, a continuation-in-part of U.S. patent application Ser. No. 16/927,886 filed on Jul. 13, 2020, and a continuation-in-part of U.S. patent application Ser. No. 16/842,631 filed on Apr. 7, 2020.

TECHNICAL FIELD

Aspects of this disclosure are generally related to use of 3D imaging.

INTRODUCTION

There are multiple subspecialties within the field of radiology. For example, the subspecialties include: neuroradiology; nuclear medicine; musculoskeletal radiology; cardiac radiology; and mammography. An imaging examination such as a CT scan of the chest, abdomen and pelvis can contain multiple abnormalities. For example, there could be an abnormality of the spine, which would best be evaluated by a neuroradiologist and an abnormality of the liver, which would best be evaluated by an abdominal imaging radiologist.

SUMMARY

All examples, aspects and features mentioned in this document can be combined in any technically conceivable way.

This patent improves upon 3D viewing of images. Specifically, it provides a process for multi-user viewing of virtual objects in mixed reality by optimizing the display to all users. More specifically, techniques disclosed herein allow a virtual object manipulated by a first user to be displayed in an eye appealing fashion to a second user.

The preferred embodiment is for a first user to be dominant and the second user to be non-dominant. The first user can be an experienced, well trained user, such as an attending radiologist who performs rotation, zooming and adjusting the appearance of the virtual object. The second user can be a novice and watch the first user expert. The method comprises: performing rendering, for the first user, based on the first user's first set of viewing parameters; monitoring for presence of a predetermined criterion of a first user; and performing rendering, for a second user, comprising: during a time epoch when the predetermined criterion of the first user is not present, performing rendering, for the second user, based on the second user's set of viewing parameters; and during a time epoch when the predetermined criterion of the first user is present, performing rendering, for the second user, based on at least one of the first user's first set of viewing parameters Some embodiments comprise wherein the first user's viewing parameter comprises a viewpoint. Some embodiments comprise wherein the first user's viewing parameter comprises a viewing angle. Some embodiments comprise wherein the first user's viewing parameter comprises an image processing status of a volume of interest. Some embodiments comprise wherein the predetermined criterion is based on a distance of movement of at least one of the group consisting of: the first user's viewpoint; a geo-registered tool; and a digital object. Some embodiments comprise wherein the predetermined criterion is based on a rotation of at least one of the group consisting of: an orientation of the first user's viewing angle; an orientation of a geo-registered tool; and an orientation of a digital object.

Some embodiments comprise wherein the predetermined criterion is based on a rate of movement of at least one of the group consisting of: the first user's viewpoint; a geo-registered tool; and a digital object.

Some embodiments comprise wherein the predetermined criterion is based on a rate of rotation of at least one of the group consisting of: an orientation of the first user's viewing angle; an orientation of a geo-registered tool; and an orientation of a digital object.

Some embodiments comprise wherein the predetermined criterion is based on image manipulation of a virtual object wherein image manipulation of a virtual object comprises at least one of the group comprising: filtering; adjusting the brightness; adjusting the contrast; and visual enhancement features.

Some embodiments comprise wherein the first user causes the first user's virtual object to be moved relative to the first user's HDU which causes the second user's virtual object to be moved relative to the second user's HDU. Some embodiments comprise applying a time delay from a first time point wherein the first user's virtual object is moved relative to the first user's HDU to a second time point wherein the second user's virtual object is moved relative to the second user's HDU. Some embodiments comprise wherein utilizing a smoothing algorithm on the path of the second user's virtual object.

Some embodiments comprise monitoring for presence of a predetermined criterion of the second user; and perform rendering, for the first user, comprising: during a time epoch when the predetermined criterion of the second user is not present, performing rendering, for the first user, based on the first user's set of viewing parameters; and during a time epoch when the predetermined criterion of the second user is present, performing rendering, for the first user, based on at least one of the second user's first set of viewing parameters.

Some embodiments comprise utilizing an eye tracking system for the first user; and presenting a digital object on the second user's virtual object at a location where a first user is looking.

Some embodiments comprise wherein the first user performs a deformation to the first user's virtual object and wherein the second user can visualize the deformation to the second user's virtual object. Some embodiments comprise wherein the first user's virtual object is displayed with a first visual representation adjustment logic and wherein the second user's virtual object is displayed with a second visual representation adjustment logic. Some embodiments comprise wherein the first user uses a virtual tool to modify the first user's virtual object and wherein the second user's virtual object is modified.

Some embodiments comprise wherein the first user uses a geo-registered tool to modify the first user's virtual object and wherein the second user's virtual object is modified.

Some embodiments comprise computer-readable storage device comprising: instructions which, when executed by a computer, cause the computer to carry out the steps of: performing rendering, for the first user, based on the first user's first set of viewing parameters; monitoring for presence of a predetermined criterion of a first user; and performing rendering, for a second user, comprising: during a time epoch when the predetermined criterion of the first user is not present, performing rendering, for the second user, based on the second user's set of viewing parameters; and during a time epoch when the predetermined criterion of the first user is present, performing rendering, for the second user, based on at least one of the first user's first set of viewing parameters.

Some embodiments comprise an apparatus comprising: an IO device; and an image processor in communication with the IO device, the image processors comprising a program stored on computer-readable non-transitory media, the program comprising: instructions that perform rendering, for the first user, based on the first user's first set of viewing parameters; instructions that monitor for presence of a predetermined criterion of a first user; and instructions that perform rendering, for a second user, comprising: during a time epoch when the predetermined criterion of the first user is not present, performing rendering, for the second user, based on the second user's set of viewing parameters; and during a time epoch when the predetermined criterion of the first user is present, performing rendering, for the second user, based on at least one of the first user's first set of viewing parameters.

BRIEF DESCRIPTION OF THE FIGURES

FIG. 5A illustrates a first user's coordinates over time wherein the first user changes viewpoints.

FIG. 5B illustrates a second user's coordinates over time wherein the second user sees a change in virtual object position.

FIG. 7 illustrates advanced techniques to determine filter verses share.

FIG. 10A illustrates a first user's viewpoints at nine different time points.

FIG. 10B illustrates locations of a virtual object as seen by a second user at 9 time points.

FIG. 11A illustrates a first user's viewpoints at nine different time points.

FIG. 11B illustrates locations of a virtual object as seen by a second user at 9 time points.

FIG. 13A illustrates a volume viewed by a first user at a first time point wherein the first user is dominant and is viewing the heart and great vessels.

FIG. 13B illustrates a second user's view through the HDU at the first time point, which shows the image of the heart.

FIG. 13C illustrates wherein the first user performs image manipulation of cutting off the great vessels to see the aortic and pulmonary valves at a second time point.

FIG. 13D illustrates the second user's view through the HDU at the second time point, which shows cutting off the great vessels to see the aortic and pulmonary valves at the second time point.

FIG. 13E illustrates wherein the first user has removed the aorta and pulmonary artery at a third time point.

FIG. 13F illustrates the second user's view through the HDU at the third time point, which shows removing of the great vessels.

FIG. 16 illustrates advanced techniques to enhance viewing for user 1 or user 2.

FIG. 18A illustrates a first user's fixation locations at nine time points, which are spread out.

FIG. 18B illustrates a lack of a digital object being displayed to the second user at nine time points, which corresponds to FIG. 18A.

FIG. 18C illustrates a first user's fixation locations at nine time points, which are in close proximity.

FIG. 18D illustrates a digital object being displayed to the second user at three time points.

FIG. 19A illustrates a zoomed in image of a virtual object of a solid mass from which a first user is focusing on the outer surface of the mass.

FIG. 19B illustrates what a first user would see through a HDU.

FIG. 19C illustrates a zoomed in image of a virtual object of a solid mass from which a second user is focusing on the inner portions of the solid mass.

FIG. 19D illustrates what a second user would see through a HDU.

FIG. 19E illustrates a zoomed in image of a virtual object of a solid mass from which a third user is focusing on a section of the solid mass.

FIG. 19F illustrates what a third user would see through a HDU.

FIG. 20A illustrates a first user at a first time point.
FIG. 20B illustrates a second user at a first time point.
FIG. 20C illustrates a first user at a second time point.
FIG. 20D illustrates a second user at a second time point.

DETAILED DESCRIPTIONS

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Figure 1:
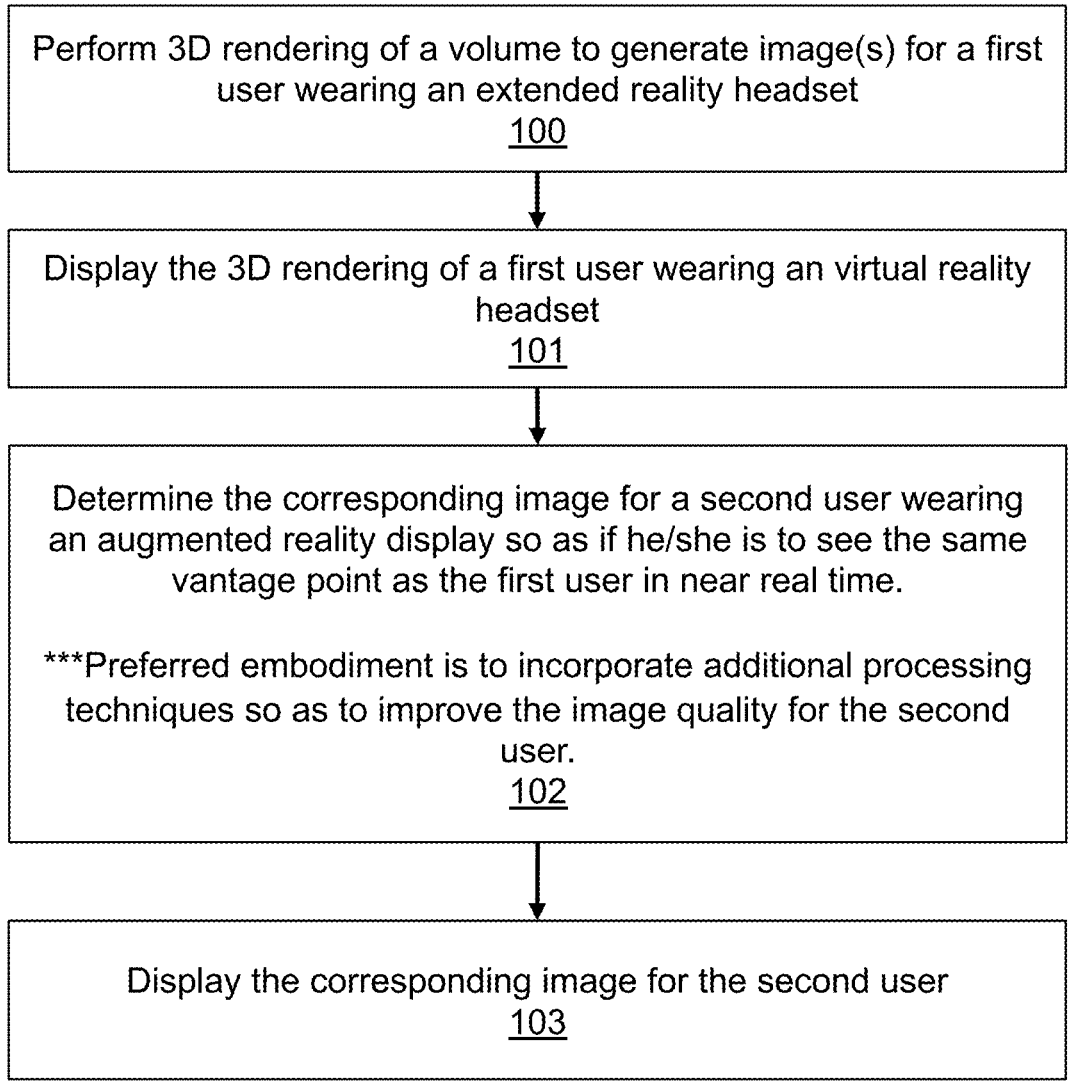
FIG. 1 illustrates generating an optimized mirrored view for a second user.

FIG. 1 illustrates generating an optimized mirrored view for a second user. 100 illustrates the processing block of performing 3D rendering of a volume to generate image(s) for a first user wearing an extended reality headset. For example, a first user is viewing a virtual object on a virtual reality (VR) head display unit (HDU). 101 illustrates the processing block of displaying the 3D rendering of a first user wearing an virtual reality headset. 102 illustrates the processing block of determining the corresponding image for a second user wearing an augmented reality display so as if he/she is to see the same vantage point as the first user in near real time. For example, a second user is wearing a mixed reality (MR) HDU. Thus, in this example, the VR viewing of an object is converted to an MR view of an object. Note is made that the preferred embodiment is to incorporate additional processing techniques so as to improve the image quality for the second user. A perfectly mirrored display would make the second user dizzy. Therefore, this additional processing step is very critical for creating an eye appealing image for the second user. 103 illustrates the processing block of displaying the corresponding image for the second user. Thus, a first user wearing a VR HDU could move his or her head (thereby changing the left eye viewpoint and the right eye viewpoint) to see a different viewpoint and viewing angle. This could cause the second user to view the rotation and translation of the virtual object.

Figure 2A:
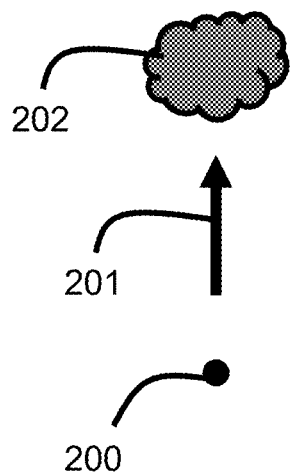
FIG. 2A illustrates a first user's viewpoint, a viewing angle, and a virtual object in a first orientation at a first time point.

FIG. 2A illustrates a first user's viewpoint, a viewing angle, and a virtual object in a first orientation at a first time point. Note that a single view point is shown, but a left eye viewpoint and right eye viewpoint can also be used. Also, note that a single viewing angle is shown, but a left eye viewing angle and a right eye viewing angle can also be used. This is discussed in U.S. Pat. No. 8,384,771, METHOD AND APPARATUS FOR THREE DIMENSIONAL VIEWING OF IMAGES, which is incorporated by reference in its entirety. A convergence point can also be used, as described by U.S. Pat. No. 9,349,183, METHOD AND APPARATUS FOR THREE DIMENSIONAL VIEWING OF IMAGES, which is incorporated by reference in its entirety. 200 illustrates the first user's viewpoint at the first time point. 201 illustrates the first user's viewing angle at the first time point. 202 illustrates the virtual object in a first orientation at the first time point.

Figure 2B:
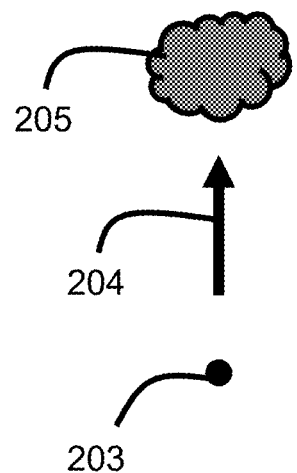
FIG. 2B illustrates a second user's viewpoint, a viewing angle, and a virtual object in a first orientation at a first time point.

FIG. 2B illustrates a second user's viewpoint, a viewing angle, and a virtual object in a first orientation at a first time point. Note that in this embodiment, the second user's rendered image is set to match the first user. 203 illustrates the second user's viewpoint at the first time point. 204 illustrates the second user's viewing angle at the first time point. 205 illustrates the virtual object in a first orientation at the first time point.

Figure 2C:
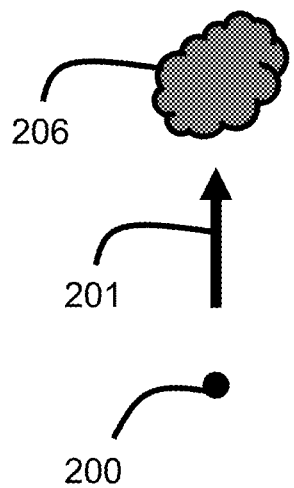
FIG. 2C illustrates the first user's viewpoint, the view angle, and the virtual object in a second orientation at a second time point.

FIG. 2C illustrates the first user's viewpoint, the view angle, and the virtual object in a second orientation at a second time point. 200 illustrates the first user's viewpoint at the second time point. 201 illustrates the first user's viewing angle at the second time point. 206 illustrates the virtual object in a second orientation at the second time point. Note that in this example, the first user caused the virtual object to change orientation from a first orientation 202 to a second orientation 206 via an input. For example, using the Depth-3-Dimensional (D3D) system, the Oculus Rift-S headset is used along with the Oculus Touch controllers. See www.d3dtechnology.net and U.S. Pat. Nos. 8,384,771, 9,349,183, 9,473,766, 9,980,691 and 10,795,457. The D3D system allows the user to reach one's hand out and grab a virtual object and then move the object through wrist and arm movements to the desired location and orientation.

Figure 2D:
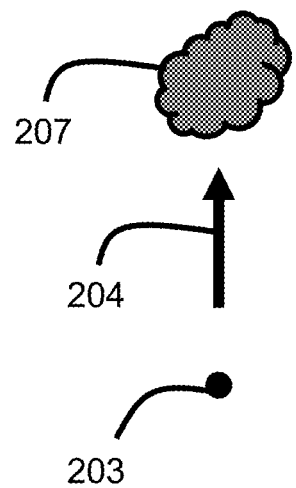
FIG. 2D illustrates the second user's viewpoint, the view angle, and the virtual object in a second orientation at a second time point.

FIG. 2D illustrates the second user's viewpoint, the view angle, and the virtual object in a second orientation at a second time point. 200 illustrates the second user's viewpoint at the second time point. 201 illustrates the second user's viewing angle at the second time point. 206 illustrates the virtual object in a second orientation at the second time point. Note that in this embodiment, the second user's rendered image is set to match the first user. Note that in this example, the virtual object changed orientation from a first orientation 205 to a second orientation 207 so that the second user could see what the first user was looking at. This is useful because it would allow the second user (e.g., a junior radiology resident) to observe the first user (e.g., attending radiologist) view a lesion. Thus, a watch and learn approach can be utilized. In other words, for the second user, no change in viewpoint(s), no change in viewing angle(s), and no changes in gaze direction are performed, but the virtual object is rotated such that the second user sees what the first user sees.

Figure 3A:
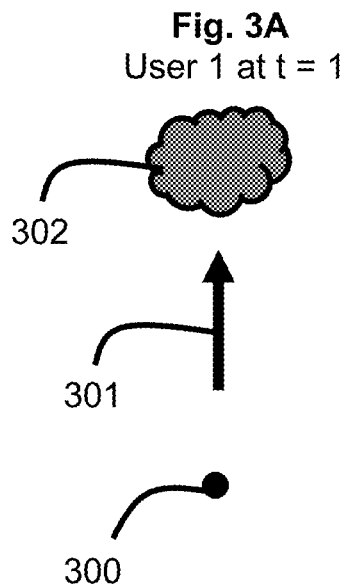
FIG. 3A illustrates a first user's first viewpoint, a first viewing angle, and a virtual object in an orientation at a first time point.

FIG. 3A illustrates a first user's first viewpoint, a first viewing angle, and a virtual object in an orientation at a first time point. Note that a single view point is shown, but a left eye viewpoint and right eye viewpoint can also be used. Also, note that a single viewing angle is shown, but a left eye viewing angle and a right eye viewing angle can also be used. This is discussed in U.S. Pat. No. 8,384,771, METHOD AND APPARATUS FOR THREE DIMENSIONAL VIEWING OF IMAGES, which is incorporated by reference in its entirety. A convergence point can also be used, as described by U.S. Pat. No. 9,349,183, METHOD AND APPARATUS FOR THREE DIMENSIONAL VIEWING OF IMAGES, which is incorporated by reference in its entirety. 300 illustrates the first user's first viewpoint at the first time point. 301 illustrates the first user's first viewing angle at the first time point. 302 illustrates the virtual object in an orientation at the first time point.

Figure 3B:
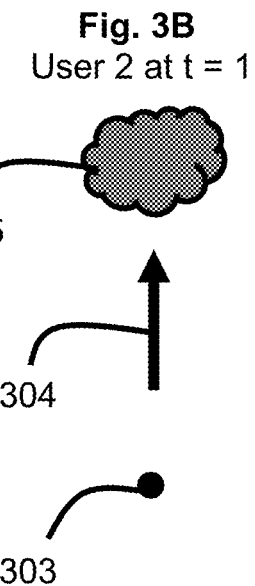
FIG. 3B illustrates a second user's viewpoint, viewing angle, and a virtual object in a first orientation at a first time point.

FIG. 3B illustrates a second user's viewpoint, viewing angle, and a virtual object in a first orientation at a first time point. Note that in this embodiment, the second user's rendered image is set to match the first user. 303 illustrates the second user's viewpoint at the first time point. 304 illustrates the second user's viewing angle at the first time point. 305 illustrates the virtual object in a first orientation at the first time point.

Figure 3C:
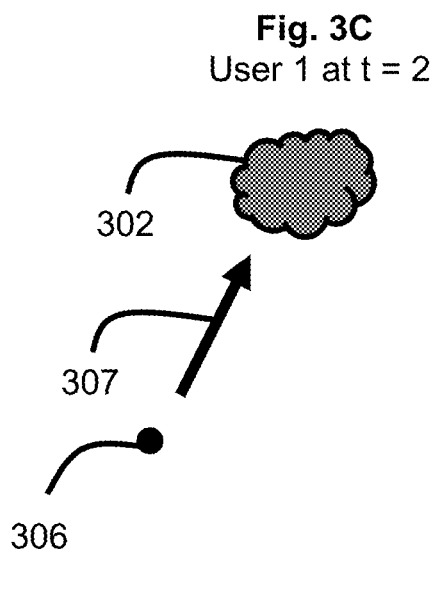
FIG. 3C illustrates the first user's second viewpoint, a second viewing angle, and the virtual object in the same orientation as in FIG. 3A at a second time point.

FIG. 3C illustrates the first user's second viewpoint, a second viewing angle, and the virtual object in the same orientation as in FIG. 3A at a second time point. This would be equivalent to moving the user's head and looking a different direction. 306 illustrates the first user's second viewpoint at the second time point. 307 illustrates the first user's second viewing angle at the second time point. 302 illustrates the virtual object in the same orientation as in FIG. 3A at the second time point. Note that in this example, the first user caused moved his/her head, but was still looking at the same virtual object. For example, this can be achieved by using the Depth-3-Dimensional (D3D) system, the Oculus Rift-S headset. See www.d3dtechnology.net and U.S. Pat. Nos. 8,384,771, 9,349,183, 9,473,766, 9,980,691 and 10,795,457. The D3D system allows the user to move one's head and turn one's head to achieve a different vantage point on the object.

Figure 3D:
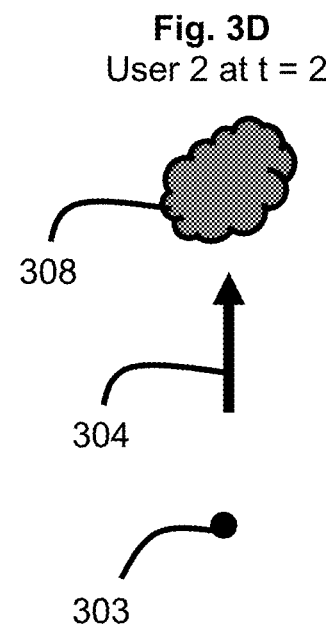
FIG. 3D illustrates the second user's viewpoint, viewing angle, and the virtual object in a second orientation at a second time point.

FIG. 3D illustrates the second user's viewpoint, viewing angle, and the virtual object in a second orientation at a second time point. Note that in this embodiment, the second user's rendered image is set to match the first user. 303 illustrates the second user's viewpoint at the second time point. 304 illustrates the second user's viewing angle at the second time point. 308 illustrates the virtual object in a second orientation at the second time point. Thus, the object would be rotated so that the second user could see where the first user is looking. Note that in this example, the virtual object changed orientation from a first orientation 305 to a second orientation 307 so that the second user could see what the first user was looking at. This is useful because it would allow the second user (e.g., a junior radiology resident) to observe the first user (e.g., attending radiologist) view a lesion. Thus, a watch and learn approach can be utilized. In other words, for the second user, no change in viewpoint(s), no change in viewing angle(s), and no changes in gaze direction are performed, but the virtual object is rotated such that the second user sees what the first user sees.

Figure 4A:
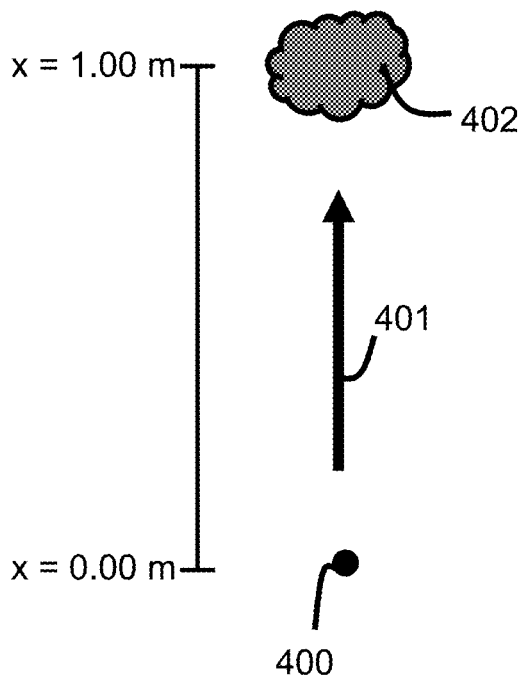
FIG. 4A illustrates a first user's first viewpoint, viewing angle, and a virtual object in an orientation at a first time point.

FIG. 4A illustrates a first user's first viewpoint, viewing angle, and a virtual object in an orientation at a first time point. Note that a single view point is shown, but a left eye viewpoint and right eye viewpoint can also be used. Also, note that a single viewing angle is shown, but a left eye viewing angle and a right eye viewing angle can also be used. This is discussed in U.S. Pat. No. 8,384,771, METHOD AND APPARATUS FOR THREE DIMENSIONAL VIEWING OF IMAGES, which is incorporated by reference in its entirety. A convergence point can also be used, as described by U.S. Pat. No. 9,349,183, METHOD AND APPARATUS FOR THREE DIMENSIONAL VIEWING OF IMAGES, which is incorporated by reference in its entirety. 400 illustrates the first user's first viewpoint at the first time point, which is located at x=0.00 m on a reference marker in physical space. 401 illustrates the first user's viewing angle at the first time point. 402 illustrates the virtual object in an orientation at the first time point, which is located at x=1.00 m on a reference marker in physical space.

Figure 4B:
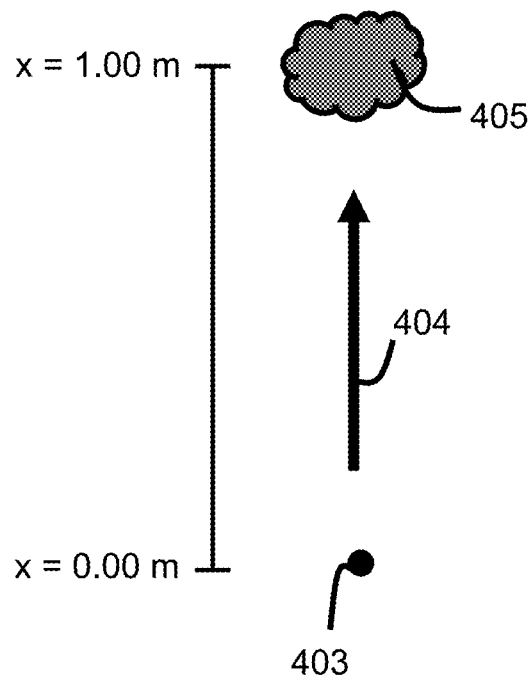
FIG. 4B illustrates a second user's viewpoint, viewing angle, and a virtual object in a first orientation at a first time point.

FIG. 4B illustrates a second user's viewpoint, viewing angle, and a virtual object in a first orientation at a first time point. Note that in this embodiment, the second user's rendered image is set to match the first user. 403 illustrates the second user's viewpoint at the first time point, which is located at x=0.00 m on a reference marker in physical space. 404 illustrates the second user's viewing angle at the first time point. 405 illustrates the virtual object in a first orientation at the first time point, which is located at x=1.00 m on a reference marker in physical space.

Figure 4C:
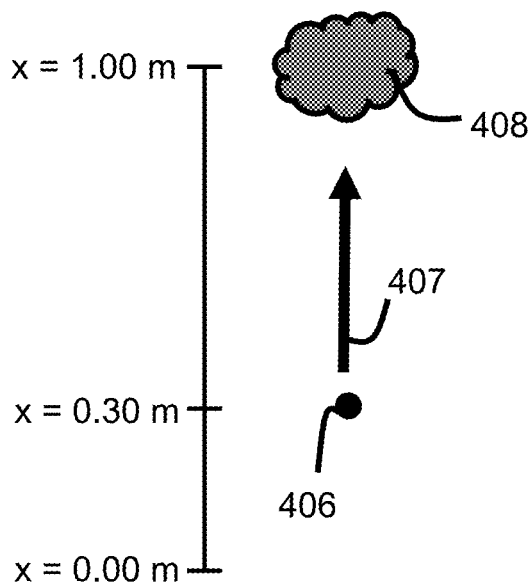
FIG. 4C illustrates the first user's second viewpoint, a viewing angle, and the virtual object in the same location and orientation in physical space as in FIG. 4A at a second time point.

FIG. 4C illustrates the first user's second viewpoint, a viewing angle, and the virtual object in the same location and orientation in physical space as in FIG. 4A at a second time point. This would be equivalent to moving the user's head forward in physical space (e.g., takes a step forward closer to the virtual object). 406 illustrates the first user's second viewpoint at the second time point, which is located at x=0.30 m on a reference marker in physical space. 407 illustrates the first user's second viewing angle at the second time point. 408 illustrates the virtual object in the same orientation and location as in FIG. 4A at the second time point, which is located at x=1.00 m on a reference marker in physical space.

Note that in this example, the first user moved his/her head, but was still looking at the same virtual object. For example, this can be achieved by using the Depth-3-Dimensional (D3D) system, the Oculus Rift-S headset. See www.d3dtechnology.net and U.S. Pat. Nos. 8,384,771, 9,349,183, 9,473,766, 9,980,691 and 10,795,457. The D3D system allows the user to move one's head (e.g., lean forward on chair, take one step forward) relative to the virtual object.

Figure 4D:
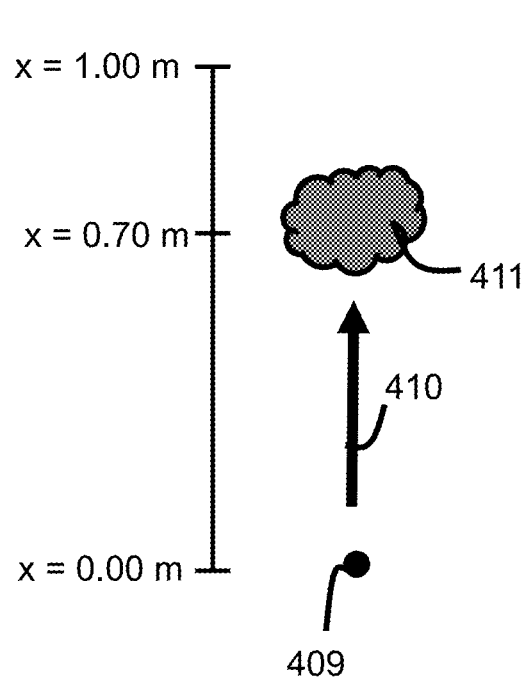
FIG. 4D illustrates the second user's viewpoint, viewing angle, and the virtual object in a second location in physical space at a second time point.

FIG. 4D illustrates the second user's viewpoint, viewing angle, and the virtual object in a second location in physical space at a second time point. Note that in this embodiment, the second user's rendered image is set to match the first user. 409 illustrates the second user's viewpoint at the second time point, which is located at x=0.00 m on a reference marker in physical space. It should be noted that the first user moved his/her head in physical space at the second time point and the second user did not move his/her head in physical space at the second time point. 410 illustrates the second user's viewing angle at the second time point. 411 illustrates the virtual object in a second location at the second time point, which is located at x=0.70 m on a reference marker in physical space. Thus, the object would be moved so that the second user could see the virtual object with a similar vantage point as the first user. Note that in this example, the virtual object changed location from a first location 404 to a second location 411 so that the second user could see what the first user was looking at. Therefore, at the second time point, the first user's viewpoint changed in physical space whereas the second user's viewpoint did not change in physical space. In addition, at the second time point, the first user's virtual object did not change in physical space whereas the second user's virtual object did change in physical space. This is useful because it would allow the second user (e.g., a junior radiology resident) to observe the first user (e.g., attending radiologist) view a lesion. Thus, a watch and learn approach can be utilized. In other words, for the second user, no change in viewpoint(s), no change in viewing angle(s), and no changes in gaze direction are performed, but the virtual object is changed in physical space such that the second user sees what the first user sees.

FIG. 5A illustrates a first user's coordinates over time wherein the first user changes viewpoints. A table is illustrated. The first column illustrates time points. The second column illustrates the viewpoints of the first user. Note that in this example, the first user is moving his head closer to the location of the virtual object. The third column shows that the position of the virtual object does not change over time.

FIG. 5B illustrates a second user's coordinates over time wherein the second user sees a change in virtual object position. A table is illustrated. The first column illustrates time points. The second column illustrates the viewpoints of the second user. Note that in this example, the second user does not move his head. The third column shows that the position of the virtual object does changes over time such that it moves closer to the second user.

Figure 6:
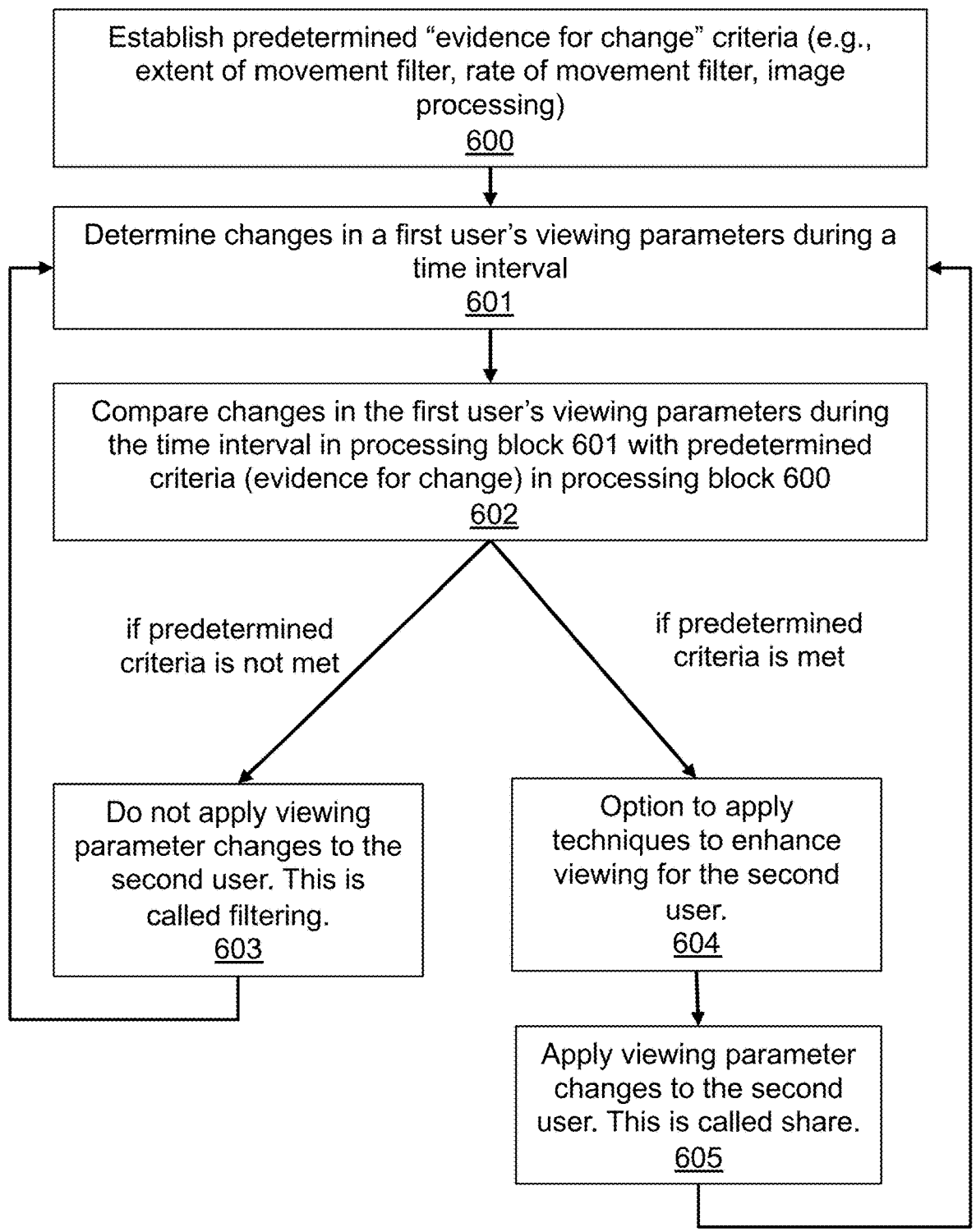
FIG. 6 illustrates applying a filter to determine whether adjustments to the second user's image should be performed.

FIG. 6 illustrates applying a filter to determine whether adjustments to the second user's image should be performed. 600 illustrates a processing block comprising establishing predetermined "evidence for change" criteria (e.g., extent of movement filter, rate of movement filter, image processing). 601 illustrates a processing block comprising determining changes in a first user's viewing parameters during a time interval. 602 illustrates a processing block comprising comparing changes in the first user's viewing parameters during the time interval in processing block 601 with predetermined criteria (evidence for change) in processing block 600. 603 illustrates a processing block, which occurs if predetermined criteria for change is not met, comprising not applying viewing parameter changes to the second user. Thus, some changes in the first user's viewing parameters (e.g., small movements of a first user's head) will not manifest as changes to the second user's viewing experience. After processing block 603, subsequently processing block 601 is performed. 604 illustrates a processing block, which occurs if predetermined criteria is met, comprising an option to apply techniques to enhance viewing for the second user. For example, an arrow may appear above a virtual object. For example, delay techniques and smoothing techniques may be applied. 605 illustrates a processing block of applying viewing parameter changes to the second user. For example, a virtual object is brought closer to the second user. Thus, some of the changes in the first user's viewing parameters would manifest as changes in the viewing parameters of the second user (e.g., a virtual object moved by the first user is brought closer to the second user). Additionally, some changes in the first user's viewing parameters would not manifest as changes in the viewing parameters of the second user (e.g., small movements in the first user's head position would not change viewing parameters of the second user)

FIG. 7 illustrates advanced techniques to determine filter verses share. As previously discussed, an action by a first user wherein a viewing parameter is changed can either be filtered (not manifest as a change in viewing parameter for a second user) or can share (manifest as a change in viewing parameter for the second user).

This section is a key point of novelty in this patent. A series of predetermined criteria can be used to determine which changes in viewing parameters of a first user translate to changes in viewing parameters of a second user and which changes in viewing parameters of a first user do not translate to changes in viewing parameters for a second user.

Part 1. Statement of Problems with sharing all viewing parameters of a first user to a second user.

First, consider the problem a second user will encounter if a first user has if he performs small head movements. If a first user moves his head small distances, it is desirable for the rendering engine to immediately provide new images at a high refresh rate (e.g., 60 Hz) so as to account for the first user's small head movements. Displaying all changes of the rendered image for the first user to the second user will cause a second user to see the mass appearing to wobble (in accordance with the first user's small head movements). This would cause it to be difficult for the second user to perform image analysis thereof and would also likely cause dizziness for the second user. Further, it would not be eye appealing to the second user, which is of course the goal. Discussed below is a point of novelty wherein extent of movement acts as a predetermined criteria, which can be used to determine whether to filter Second, consider the problem a second user will encounter if a first user performs rapid movements. Additionally, if a first user quickly brought the volume closer to them, that action would of course be natural and non-dizzying to the first user because it is the first user who used his own will power to move the item closer at a fast rate. However, if the volume suddenly and quickly was brought closer to the second user, this is irritating, jarring and not eye appealing. In fact, it might even scare the second user. Additionally, if the first user grabs a virtual object and quickly snaps his wrist while using the Oculus Touch controllers on the current version 3.1 of the D3D imaging system (www.d3dtechnology.net), the quick response time of the system is desirable for the first user; however, displaying such a quick rotation of the mass to the second user would cause nausea.

Third, consider the problem a second user will encounter if a first user performs too many image processing steps. If a first user is playing with the visual representation adjustment logic, such as transparency adjustment per U.S. Pat. No. 10,586,400, PROCESSING 3D MEDICAL IMAGES TO ENHANCE VISUALIZATION, which is incorporated by reference in its entirety. Assume that the user is performing rapid changes in the visual representation. Such rapid changes may hinder the ability of a second user to perform analysis of the image because the image will appear to flicker or flash. As a result, an emulator on HDUs can cause dizziness.

Part 2. PREDETERMINED CRITERIA First, a set of factors in determining if updated view (moving or rotating the virtual objects) for the second user should be implemented. The factors include: range; rate; and, image processing step.

Part 2.1. EXTENT OF MOVEMENT CRITERIA. An innovative concept is the filtering of some (but not all) movements and actions of a first user. Note that the extent in movement criterial will be discussed at length for the head display unit, but it is equally applicable for movement of geo-registered tools and digital objects.

Consider an extent of movement criteria. The extent of movement criteria filter could be related to distance (e.g., in cm) moved or the rotation (e.g., in degrees) moved.

In this embodiment, a distance of movement cut off (wherein below the cut off, no inputs are sent to the second user) is performed and is useful because this would prevent small movements of the first user from causing a dizzy appearance to the second user. If a first user moves his head a distance of less than 5 cm, then an updated volume is not presented to the second user. If a first user moves his head a distance of 5 cm or more, then an updated volume is presented to the second user (an performed in a smooth, eye appealing fashion for the second user). This prevents small movements of the first user from causing a dizzying effect for the second user and is therefore effective.

In this embodiment, a degree of movement cut off (wherein below the cut off, no inputs are sent to the second user) is performed and is useful because this would prevent small movements of the first user from causing a dizzy appearance to the second user. If a first user changes the viewing angle (which can be done by moving the head to view a virtual object from a different perspective or rotating the virtual object) less than, for example, 20 degrees, then an updated volume is not presented to the second user. If a first user moves his head 20 degrees or more, then an updated volume is presented to the second user. This prevents small movements of the first user from causing a dizzying effect for the second user and is therefore effective.

These examples of distance of movement criteria and degree of movement criteria were discussed for HDU movement. However, the distance of movement criteria and degree of movement criteria can also be applied to geo-registered objects as well. Geo-registered tools are discussed in U.S. Pat. No. 10,712,837, USING GEO-REGISTERED TOOLS TO MANIPULATE THREE-DIMENSIONAL MEDICAL IMAGES, which is incorporated by reference in its entirety. For example, if a first user were holding a geo-registered platform, he might intentionally make small movements to improve his (first user's) viewing experience, but these small movements could be filtered out and not displayed to the second user. Therefore, the distance of movement criteria can be applied to geo-registered tools.

In addition, the distance of movement criteria and degree of movement criteria can also be applied to digital objects. Digital objects are discussed in PCT/US19/47891, A VIRTUAL TOOL KIT FOR 3D IMAGING, which is incorporated by reference in its entirety. For example, if a first user were moving a digital object, he might intentionally make small movements to improve his (first user's) viewing experience, but these small movements could be filtered out and not displayed to the second user. Therefore, the distance of movement criteria can be applied to virtual tools.

Part 2.2. RATE OF MOVEMENT CRITERIA. Consider a rate of movement criteria. A rate filter could be related to distance per unit time (e.g., in cm/sec) that a HDU or virtual object is moved or the rotation of degrees per unit time (e.g., in degrees/sec) that a HDU or virtual object is moved or rotated, respectively. The rate of movement of the first user could also be modulated so as to create a more eye appealing image to the second user.

In some embodiments, a rate cut off can be applied wherein when a first user performs movements above or below a cut off level, the movements are filtered.

In some embodiments, a rate modulation is implemented (wherein above the cut off, inputs are modulated prior to being sent to the second user) is performed and is useful because this would prevent rapid movements of the first user from causing a jarring, non-eye appealing appearance to the second user.

Assume the distance per time rate cut off of 2 cm/sec. Assume a first user moves his head at a rate of 5 cm/sec over a distance of 10 cm. The movement rate of the first user of 5 cm/sec is greater than the rate cut off of 2 cm/sec. The movement rate of the virtual object can be modulated to the rate of 2 cm/sec, which will create more of an eye appealing image. This prevents rapid movements of the first user from causing a dizzying effect for the second user and is therefore useful. An second user preference settings can be implemented (e.g., acceleration and deceleration implemented, 0-1 seconds move at slow rate of 0.5 cm/sec, 1-2 seconds medium rate of 1.0 cm/sec, 2.0-5.5 seconds fast rate of 2.0 cm/sec, 5.5-6.5 seconds medium rate of 1.0 cm/sec, 6.5-7.5 sec slow rate of 0.5 cm/sec). In this example, the first user moved the virtual object the distance of 10 cm over 2 seconds at a rate of 5 cm/sec. The rate filter was implemented and the object was moved on the second user's display over 7.5 seconds. This rate filter causes a more eye appealing image.

In some embodiments, a degrees per time cut off for modulation (wherein above the cut off, inputs are modulated prior to being sent to the second user) is performed and is useful because this would prevent rapid rotations of the virtual object of the first user from causing a jarring, non-eye appealing appearance to the second user.

Assume the rotation per time rate cut off of 10 degrees/sec. Assume a first user rotated the object 90 degrees over 1 second. First, the movement rate of the first user of 90 degrees/sec is greater than the rate cut off of 10 degrees/sec. The movement rate of the virtual object can be modulated to the rate of 10 degrees/sec, which will create more of an eye appealing image. This prevents rapid movements of the first user from causing a dizzying effect for the second user and is therefore useful. A second user preference settings can be implemented (e.g., acceleration and deceleration implemented if desired) at a maximum rate of 10 degrees per second. Assume that the rotation goes at an average rate of 9 degrees per second (due to acceleration and deceleration). In this example, the first user moved the virtual object at a rotation rate of 90/sec over 1 second. The rate filter was implemented and the object was moved on the second user's display over 10 seconds. This rate filter causes a more eye appealing image.

Part 2.3. IMAGE MANIPULATION CRITERIA. Consider a image processing filter. A first user could apply image processing steps in rapid sequence, such as using a mouse or joystick to change the transparency. Herein is disclosed a process to improve visual analysis for a second user.

Assume a CT scan of the abdomen. A first user may adjust the grayscale (e.g., window level setting) up and down to adjust the brightness of the image. Assume the first user overshoots twice and undershoots twice and after these fine tune corrections, the desired brightness of the image is achieved. Next, assume that the first user wants to adjust the contrast and similarly narrows and widens the grayscale (e.g., window width setting). Assume that the first user overshoots twice and undershoots twice and after these fine tune corrections, the desired contrast of the image is achieved. Assume that these 8 minor corrections occur within 8 seconds and thereafter the user studies the image for 20 seconds with the established grayscale settings.

In this embodiment, a process to skip the intermediate overshoot and undershoots for both the brightness (e.g., window level) and contrast (e.g., window width) is performed and is useful because this would generate a more useful image for the second user.

In another embodiment, if a minor change (e.g., a window level change of less than 1 Hounsfield units) is performed by a first user, then no changes would be implemented for the second user.

A wide range of image manipulations can be performed. Some of these can be filtered. Others can be shared.

Figure 8:
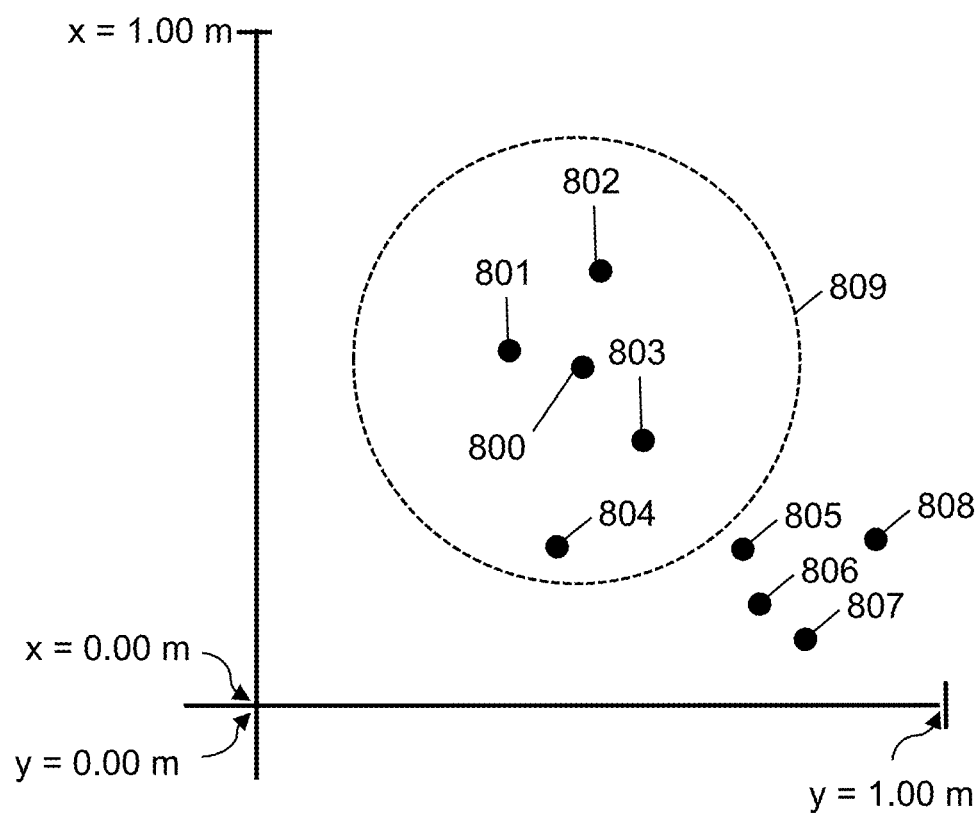
FIG. 8 illustrates using a measurement as a predetermined criteria.

FIG. 8 illustrates using a measurement as a predetermined criteria. 800 illustrates the first user's viewpoint at a first time point, which is inside of radius 810. Note that radius 810 creates a sphere (z-direction not shown). The radius acts as a predetermined criteria for movement. If the user stays inside of the sphere, no changes to the second user's viewing parameters are shown. Thus, a time point 1, no change will be made to a second user's viewing parameters. 801 illustrates the first user's viewpoint at a second time point, which is inside radius 810 and therefore a modification to a second user's viewing parameters will not be performed. 802 illustrates the first user's viewpoint at a third time point, which is inside radius 810 and therefore a modification to a second user's viewing parameters will not be performed. 803 illustrates the first user's viewpoint at a fourth time point, which is inside radius 810 and therefore a modification to a second user's viewing parameters will not be performed. 804 illustrates the first user's viewpoint at a fifth time point, which is inside radius 810 and therefore a modification to a second user's viewing parameters will not be performed. 805 illustrates the first user's viewpoint at a sixth time point, which is outside radius 810 and therefore a modification to a second user's viewing parameters will be performed. 806 illustrates the first user's viewpoint at a seventh time point, which is outside radius 810 and therefore a modification to a second user's viewing parameters will be performed. 807 illustrates the first user's viewpoint at an eighth time point, which is outside radius 810 and therefore a modification to a second user's viewing parameters will be performed. 808 illustrates the first user's viewpoint at a ninth time point, which is outside radius 810 and therefore a modification to a second user's viewing parameters will be performed.

Figure 9:
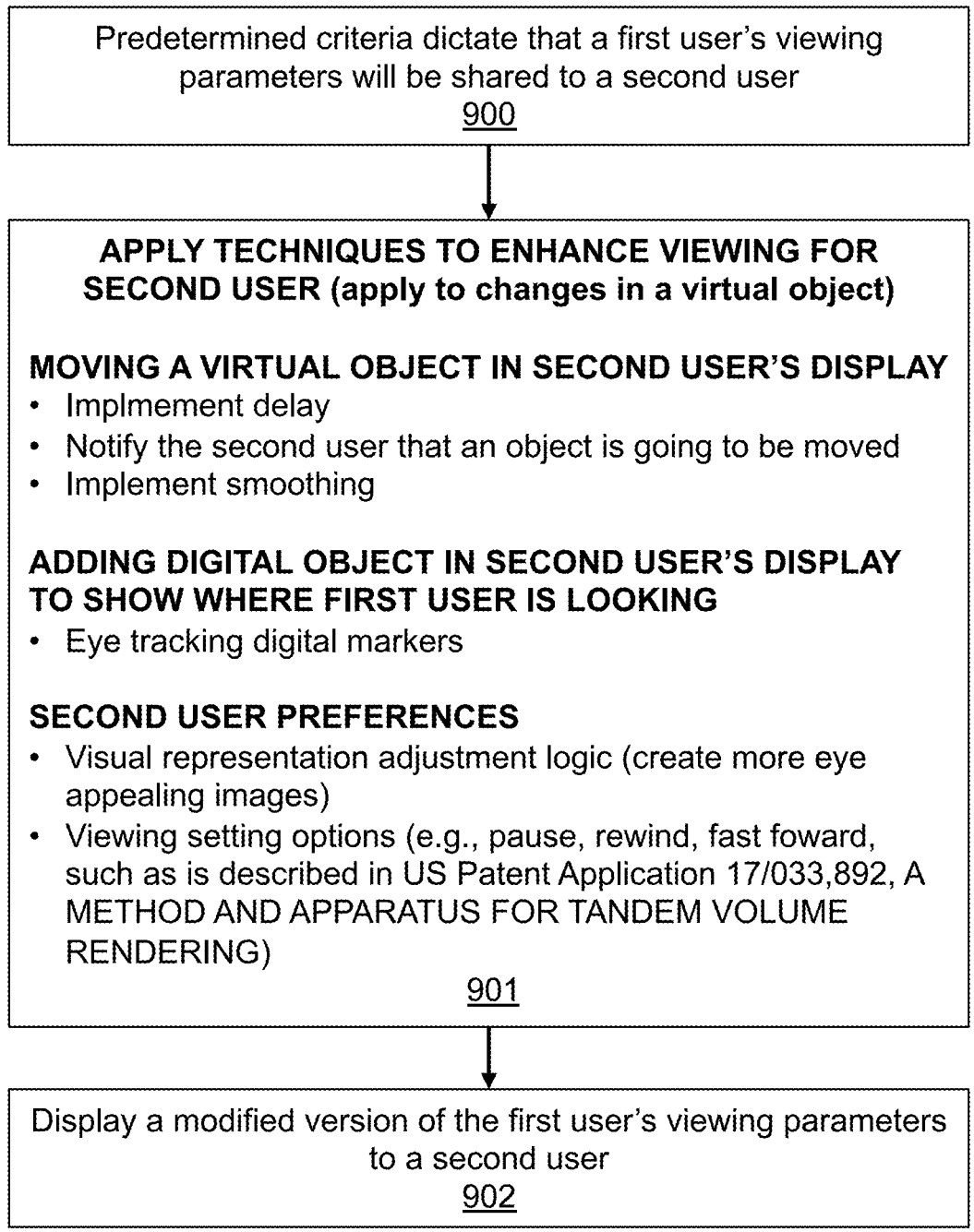
FIG. 9 illustrates advanced techniques to enhance viewing for the second user.

FIG. 9 illustrates advanced techniques to enhance viewing for the second user. 900 illustrates wherein application of predetermined criteria dictate that a first user's viewing parameters will be shared to a second user. 901 illustrates apply techniques to enhance viewing for second user. If the predetermined criteria dictate that the step is to share, then techniques to enhance viewing for the second user are applied. Some embodiments comprise moving a virtual object in second user's display. When a virtual object is moved in a second user's display, a delay of a period of time can be implemented. This allows time to apply the predetermined criteria to a first user's viewing parameters and determine whether to share or filter the first user's viewing parameters. In some embodiments, a delay is performed to wait for the first user's rapid manipulations to end. Then, once the rapid manipulations end, an eye appealing transition from the first image to the last image is generated. In this case, some of the intermediate images are not revealed to the second user. A key technique is smoothing, so that any virtual object that is moved (from the perspective of the second user). In some embodiments, a change in appearance of the mass or adjacent visual marker (e.g., arrow) could give the second user a visual notification that the mass is about to move or rotate. Some embodiments comprise adding digital object in second user's display to show where first user is looking. A delay can be implemented. Please see examples of a digital object in U.S. Pat. No. 10,712,837, USING GEO-REGISTERED TOOLS TO MANIPULATE THREE-DIMENSIONAL MEDICAL IMAGES, which is incorporated by reference in its entirety. Some embodiments comprise incorporating second user preferences to enhance the viewing experience. For example, visual representation adjustment logic (create more eye appealing images) can be adjusted, which can be performed via U.S. Pat. No. 10,586,400, PROCESSING 3D MEDICAL IMAGES TO ENHANCE VISUALIZATION, which is incorporated by reference in its entirety. Additionally, viewing setting options (e.g., pause, rewind, fast forward) and rendering techniques described in U.S. Pat. No. 10,776,989, A METHOD AND APPARATUS FOR PRIORITIZED VOLUME RENDERING, and U.S. patent application Ser. No. 17/033,892, A METHOD AND APPARATUS FOR TANDEM VOLUME RENDERING, can be performed, both of which are incorporated by reference in their entirety. 902 illustrates displaying a modified version of the first user's viewing parameters to a second user. Thus, a key point of novelty is the act of hybrid emulating while rendering.

FIG. 10A illustrates a first user's viewpoints at nine different time points. 1000 illustrates the location of first user's viewpoint at a first time point. 1001 illustrates the location of first user's viewpoint at a second time point. 1002 illustrates the location of first user's viewpoint at a third time point. 1003 illustrates the location of first user's viewpoint at a fourth time point. 1004 illustrates the location of first user's viewpoint at a fifth time point. 1005 illustrates the location of first user's viewpoint at a sixth time point. 1006 illustrates the location of first user's viewpoint at a seventh time point. 1007 illustrates the location of first user's viewpoint at an eighth time point. 1008 illustrates the location of first user's viewpoint at a ninth time point. The first user moves his head in the general trajectory towards the virtual object of interest, but also in a somewhat back and forth pattern.

FIG. 10B illustrates locations of a virtual object as seen by a second user at 9 time points. 1009 illustrates the location of a virtual object as seen by the second user at a first time point. 1010 illustrates the location of a virtual object as seen by the second user at a second time point. 1011 illustrates the location of a virtual object as seen by the second user at a third time point. 1012 illustrates the location of a virtual object as seen by the second user at a fourth time point. 1013 illustrates the location of a virtual object as seen by the second user at a fifth time point. 1014 illustrates the location of a virtual object as seen by the second user at a sixth time point. 1015 illustrates the location of a virtual object as seen by the second user at a seventh time point. 1016 illustrates the location of a virtual object as seen by the second user at an eighth time point. 1017 illustrates the location of a virtual object as seen by the second user at a ninth time point. The second user's viewpoint does not move. The second user sees the virtual object move towards him in a similar vantage point as the first user; however, it should be noted that the object moves in a smooth arc towards the second user. A smoothing technique enhances the viewing experience for the second user. To achieve the optimal viewing experience for the second user, any combination of modified viewing parameters can be implemented (e.g., changing viewpoints, changing viewing angles, changing the volume of interest, techniques disclosed in the patents and patent applications, which are incorporated by reference, etc.)

FIG. 11A illustrates a first user's viewpoints at nine different time points. 1100 illustrates the location of first user's viewpoint at a first time point. 1101 illustrates the location of first user's viewpoint at a second time point. 1102 illustrates the location of first user's viewpoint at a third time point. 1103 illustrates the location of first user's viewpoint at a fourth time point. 1104 illustrates the location of first user's viewpoint at a fifth time point. 1105 illustrates the location of first user's viewpoint at a sixth time point. 1106 illustrates the location of first user's viewpoint at a seventh time point. 1107 illustrates the location of first user's viewpoint at an eighth time point. 1108 illustrates the location of first user's viewpoint at a ninth time point. The first user moves his head in the general trajectory towards the virtual object of interest, but also in a somewhat back and forth pattern.

FIG. 11B illustrates locations of a virtual object as seen by a second user at 9 time points. 1109 illustrates the location of a virtual object as seen by the second user at a first time point, a second time point, a third time point, a fourth time point and a fifth time point. 1110 illustrates the location of a virtual object as seen by the second user at a sixth time point. 1111 illustrates the location of a virtual object as seen by the second user at a seventh time point. 1112 illustrates the location of a virtual object as seen by the second user at an eighth time point. 1113 illustrates the location of a virtual object as seen by the second user at a ninth time point. The second user's viewpoint does not move. The second user sees the virtual object move towards him in a similar vantage point as the first user; however, it should be noted that the object moves in a smooth arc towards the second user. Also note that a delay has been implemented. A smoothing technique enhances the viewing experience for the second user. To achieve the optimal viewing experience for the second user, any combination of modified viewing parameters can be implemented (e.g., changing viewpoints, changing viewing angles, changing the volume of interest, techniques disclosed in the patents and patent applications, which are incorporated by reference, etc.).

Figure 12:
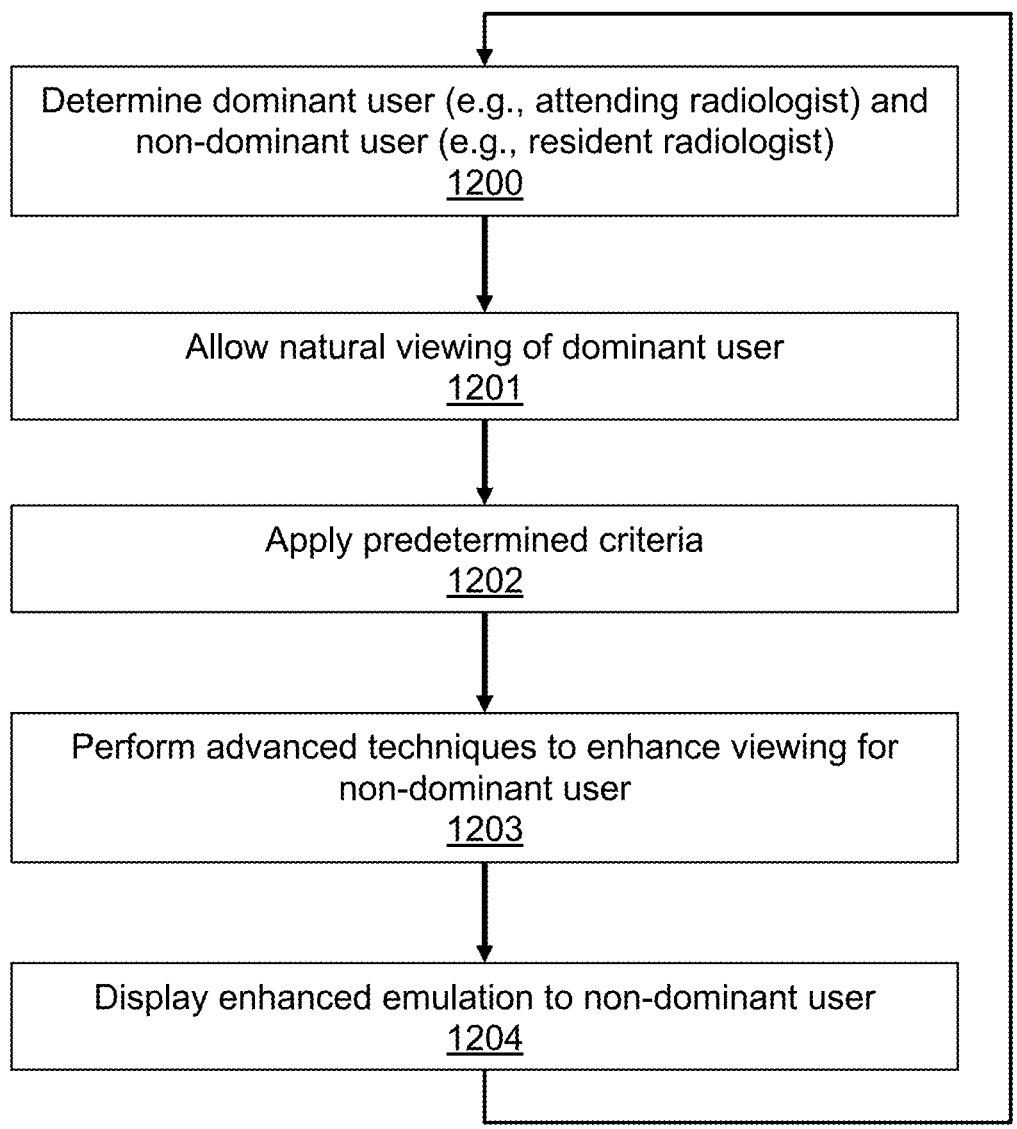
FIG. 12 illustrates a dynamic dominant system.

FIG. 12 illustrates a dynamic dominant system. 1200 illustrates determining a dominant user (e.g., attending radiologist) and non-dominant user (e.g., resident radiologist). 1201 illustrates allowing natural viewing of dominant user. Note that both the dominant user and non-dominant user are wearing HDUs. 1202 illustrates applying predetermined criteria. 1203 illustrates performing advanced techniques to enhance viewing for the non-dominant user. 1204 illustrates displaying enhanced emulation to the non-dominant user.

FIG. 13A illustrates a volume viewed by a first user at a first time point wherein the first user is dominant and is viewing the heart and great vessels. An image of the heart is shown.

FIG. 13B illustrates a second user's view through the HDU at the first time point, which shows the image of the heart.

FIG. 13C illustrates wherein the first user performs image manipulation of cutting off the great vessels to see the aortic and pulmonary valves at a second time point. This constitutes a deformation can be performed by methods disclosed in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

FIG. 13D illustrates the second user's view through the HDU at the second time point, which shows cutting off the great vessels to see the aortic and pulmonary valves at the second time point.

FIG. 13E illustrates wherein the first user has removed the aorta and pulmonary artery at a third time point.

FIG. 13F illustrates the second user's view through the HDU at the third time point, which shows removing of the great vessels.

Figure 14:
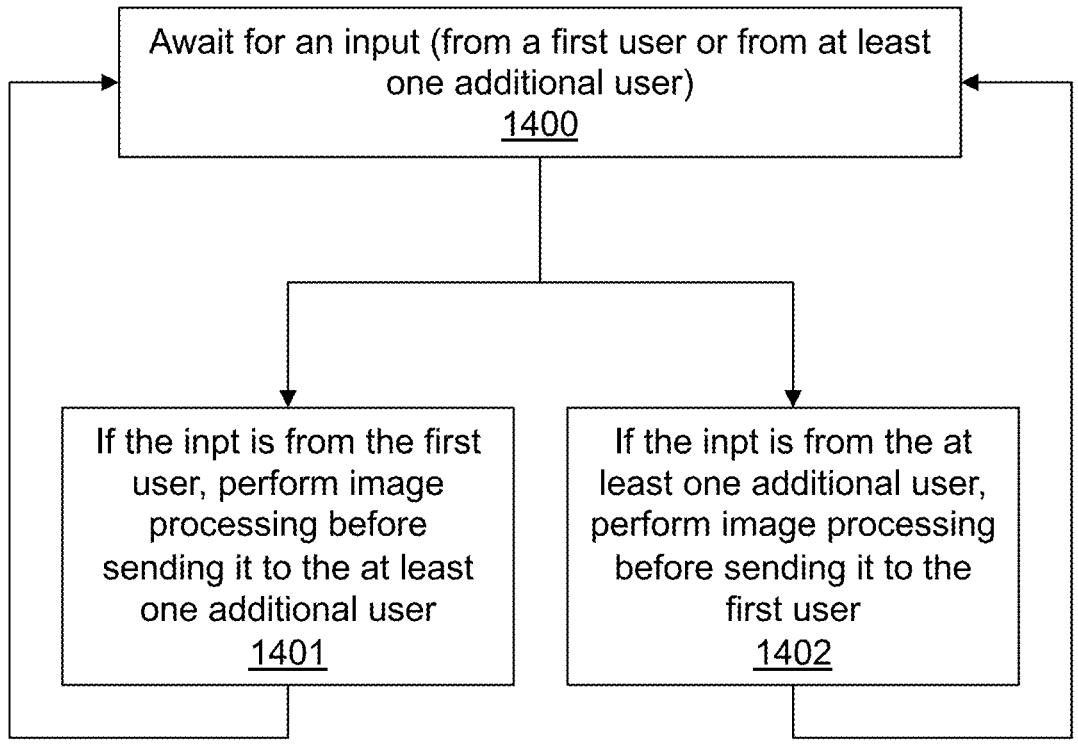
FIG. 14 illustrates interactive viewing and manipulation of a volume.

FIG. 14 illustrates interactive viewing and manipulation of a volume. 1400 illustrates a processing block of awaiting for an input (from a first user or from at least one additional user). 1401 illustrates a processing block which occurs if the input is from the first user comprising performing image processing before sending it to the at least one additional user. 1402 illustrates a processing block which occurs if the input is from the at least one additional user comprising performing image processing before sending it to the first user. To explain this, consider a situation wherein three users are viewing the same mass and are trying to determine what it is. All three users are at the same level of training and experience (e.g., first year radiology residents). During a first time period, all three residents are studying the mass from the front and no input is performed. During a second time period, the first resident performs a filtering step to see deeper layers of the mass and the imaging volume is updated for the second resident and the third resident. During a third time period, all three residents are studying the mass which has undergone image processing. During a fourth time period, the third resident performs rotation of the mass to visualize if from the top and the imaging volume is updated for the first resident and the second resident. And so on. Sometimes, a user may elect to perform image manipulation (e.g., rotation, image processing steps such as filtering, adjusting transparency, etc.), but choose not to share every step with the others. Therefore, a processing block can be utilized to share only when a user chooses to.

Figure 15:
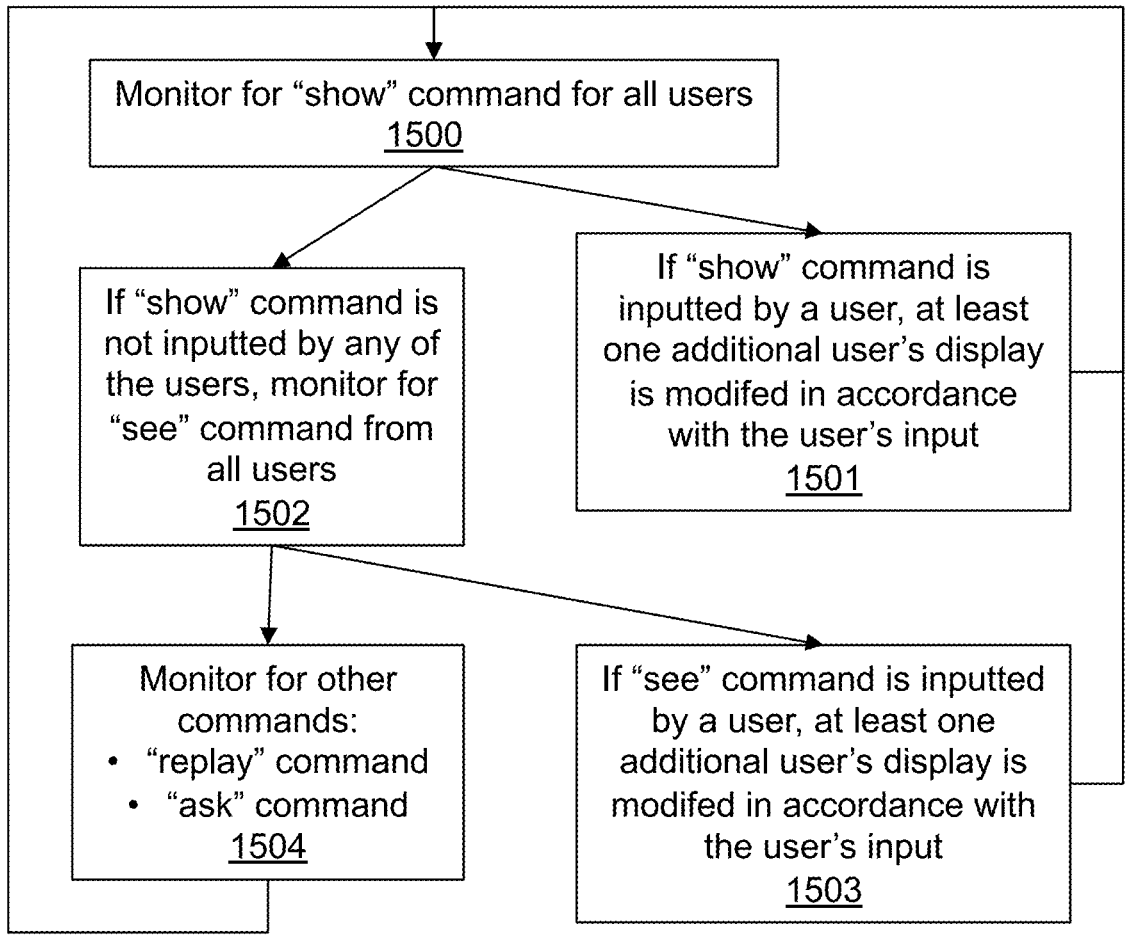
FIG. 15 illustrates a dynamic co-dominant system.

FIG. 15 illustrates a dynamic co-dominant system. 1500 illustrates monitoring for "show" command for all users. 1501 illustrates wherein if a "show" command is inputted by a user, at least one additional user's display is modified in accordance with the user's input. In some embodiments, the "show" command may be "full override". In other embodiments, the "show" command may give an option to "override". After this, return to step 1500. 1502 illustrates wherein if "show" command is not inputted, monitor for "see" command from all users. 1503 illustrates wherein if "see" command is inputted by a user, at least one additional user's display is modified in accordance with the user's input. After this, return to step 1500. 1504 illustrates monitoring for other commands: "replay" command (replays previously rendered images); "ask" command (a user may ask another user "what is this structure?" and provide an annotation, issue "show" command and receive feedback). Thus, a team work approach on a volume can be performed.

FIG. 16 illustrates advanced techniques to enhance viewing for user 1 or user 2. In some embodiments, advanced volume rendering techniques are performed. In some embodiments, an advanced volume rendering techniques called prioritized volume rendering is performed, which is performed via techniques as described in U.S. Pat. No. 10,776,989, A METHOD AND APPARATUS FOR PRIORITIZED VOLUME RENDERING, which is incorporated by reference in its entirety. In some embodiments, an advanced volume rendering technique called tandem volume rendering is performed, which is performed via techniques as described in U.S. patent application Ser. No. 17/033,892, A METHOD AND APPARATUS FOR TANDEM VOLUME RENDERING, which is incorporated by reference in its entirety. In some embodiments, an analytical step involves generating a precision sub-volume based on anatomical landmarks, which is performed via techniques as described in Ser. No. 16/927,886, A METHOD AND APPARATUS FOR GENERATING A PRECISION SUB-VOLUME WITHIN THREE-DIMENSIONAL IMAGE DATASETS, which is incorporated by reference in its entirety. In some embodiments, eye tracking techniques and other advanced imaging techniques are incorporated, which are described in U.S. patent application Ser. No. 16/842,631, A SMART SCROLLING SYSTEM, which is incorporated by reference in its entirety. In addition, eye tracking features, such as the eye tracking digital object, are also discussed in U.S. Pat. No. 10,712,837, USING GEO-REGISTERED TOOLS TO MANIPULATE THREE-DIMENSIONAL MEDICAL IMAGES, which is incorporated by reference in its entirety. In some embodiments, a dynamic deformation of a 3D dataset is performed to improve visualization of complex features and/or to perform a simulation, which is described in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety. In some embodiments, advance image processing techniques, such as double windowing, are performed, which are described in U.S. Pat. No. 10,586,400, PROCESSING 3D MEDICAL IMAGES TO ENHANCE VISUALIZATION, which is incorporated by reference in its entirety. In some embodiments, use of virtual tools are performed, which is described in PCT/US19/47891, A VIRTUAL TOOL KIT FOR 3D IMAGING, which is incorporated by reference in its entirety. In some embodiments, use of geo-registered tools are performed, which is described in U.S. Pat. No. 10,712,837, USING GEO-REGISTERED TOOLS TO MANIPULATE THREE-DIMENSIONAL MEDICAL IMAGES, which is incorporated by reference in its entirety. In some embodiments, secondary analysis of imaging findings is performed via techniques as described in PCT/US2019/023968, RADIOLOGIST ASSISTED MACHINE LEARNING, which is incorporated by reference in its entirety. In some embodiments, the secondary analysis is performed via techniques as described in Ser. No. 17/072,350, OPTIMIZED IMAGING CONSULTING PROCESS FOR RARE IMAGING FINDINGS, which is incorporated by reference in its entirety.

Figure 17A:
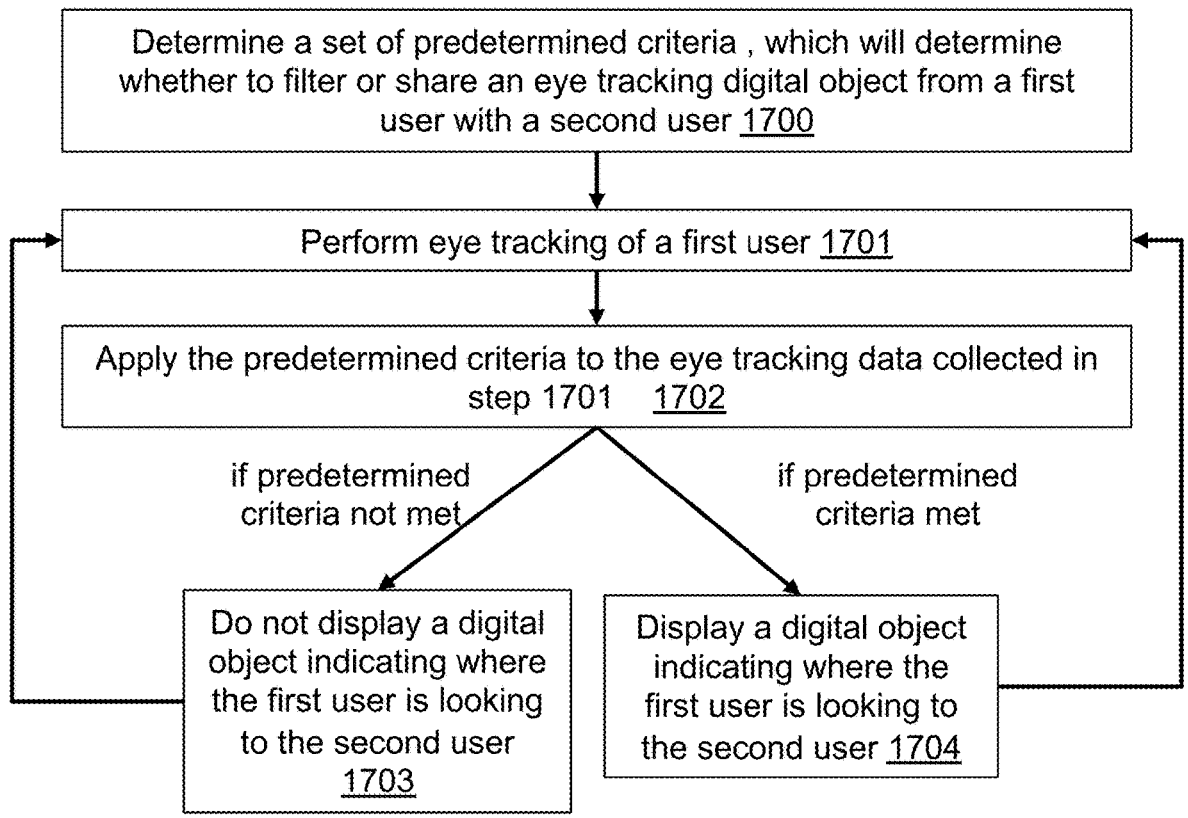
FIG. 17A illustrates an algorithm of an advanced option wherein a second user can see the location where a first user is looking.

FIG. 17A illustrates an algorithm of an advanced option wherein a second user can see the location where a first user is looking. 1700 illustrates determining a set of predetermined criteria, which will determine whether to filter or share an eye tracking digital object from a first user with a second user. Examples of predetermined criteria include, but are not limited to, the following: number of fixation locations within a region; length of time of fixation; and, facial expression of the first user. This is further described in U.S. patent application Ser. No. 16/842,631, A SMART SCROLLING SYSTEM, which is incorporated by reference in its entirety. For example, if a first user looks at an anatomic feature more than 10 times and for a total of more than 15 seconds, this combination would meet the predetermined criteria. 1701 illustrates performing eye tracking of a first user. 1702 illustrates apply the predetermined criteria to the eye tracking data collected in step 1701. 1703 illustrates not displaying a digital object indicating where the first user is looking to the second user, which is performed if the predetermined criteria in step 1700 is not met. 1704 illustrates displaying a digital object indicating where the first user is looking to the second user, which is performed if the predetermined criteria in step 1700 is met. A point of novelty is that some of the fixation locations of the first user will be filtered and other fixation locations will be shared (i.e., not filtered).

Figure 17B:
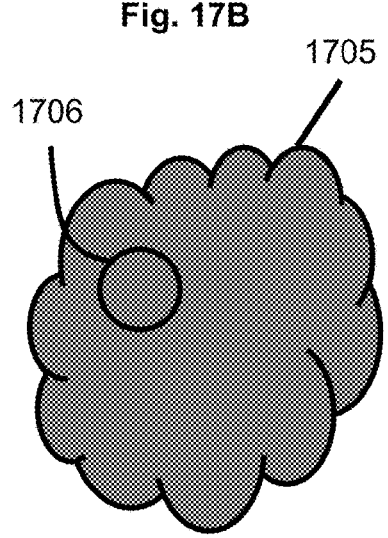
FIG. 17B illustrates a fixation location for a first user.

FIG. 17B illustrates a fixation location for a first user. 1705 illustrates a mass as viewed by a first user. 1706 illustrates a fixation location of the first user.

A HDU with eye tracking capabilities is utilized.

Figure 17C:
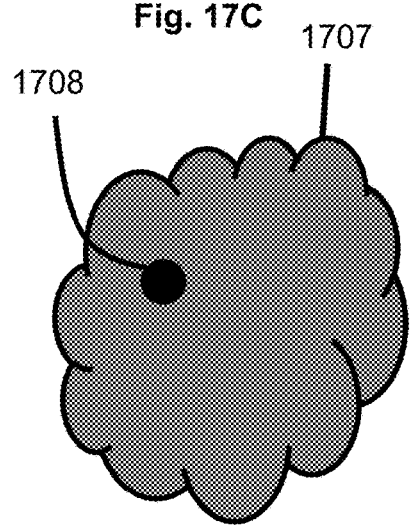
FIG. 17C illustrates display of the first user's fixation location to a second user.

FIG. 17C illustrates display of the first user's fixation location to a second user. 1707 illustrates the mass as viewed by the second user. 1708 illustrates a digital object displayed on the mass as viewed by the second user, which indicates that this is the location where the first user is currently looking. A series of user preferences can be applied. A setting of time displayed can be implemented. For example, the digital object can be displayed for 1 second and then disappear. For example, the digital object can be displayed until the second user looks at it.

FIG. 18A illustrates a first user's fixation locations at nine time points, which are spread out. 1800 illustrates a first fixation location at a first time point. 1801 illustrates a second fixation location at a second time point. 1802 illustrates a third fixation location at a third time point. 1803 illustrates a fourth fixation location at a fourth time point. 1804 illustrates a fifth fixation location at a fifth time point. 1805 illustrates a sixth fixation location at a sixth time point. 1806 illustrates a seventh fixation location at a seventh time point. 1807 illustrates a eighth fixation location at an eighth time point. 1808 illustrates a ninth fixation location at a ninth time point.

FIG. 18B illustrates a lack of a digital object being displayed to the second user at nine time points, which corresponds to FIG. 18A. Note that no eye tracking dot is displayed on the second user's display. This is because the predetermined criteria (e.g., radius) has not been met.

FIG. 18C illustrates a first user's fixation locations at nine time points, which are in close proximity. 1809 illustrates a first fixation location at a first time point. 1810 illustrates a second fixation location at a second time point. 1811 illustrates a third fixation location at a third time point. 1812 illustrates a fourth fixation location at a fourth time point. 1813 illustrates a fifth fixation location at a fifth time point. 1814 illustrates a sixth fixation location at a sixth time point. 1815 illustrates a seventh fixation location at a seventh time point. 1816 illustrates an eighth fixation location at an eighth time point. 1817 illustrates a ninth fixation location at a ninth time point.

FIG. 18D illustrates a digital object being displayed to the second user at three time points. 1818 illustrates a digital object displayed to the second user during time point seven, time point eight and time point nine. This is because the predetermined criteria (e.g., radius) has been met.

FIG. 19A illustrates a zoomed in image of a virtual object of a solid mass from which a first user is focusing on the outer surface of the mass. 1900 illustrates the solid mass, which is being worked on and processed by the first user.

FIG. 19B illustrates what a first user would see through a HDU. 1901 illustrates the HDU with a left eye display and a right eye display. 1902 illustrates the solid mass as shown on the left eye display. Note that the solid mass 102 is of greatest interest to the first user. However, the first user is also interested in what the solid mass looks like with the processing that is undergone by the second user and the third user. 1903 illustrates the solid mass as processed the second user as shown on the left eye display. 1904 illustrates the solid mass as processed the third user as shown on the left eye display. 1905 illustrates the solid mass as shown on the right eye display. 1906 illustrates the solid mass as processed the second user as shown on the right eye display. 1907 illustrates the solid mass as processed the third user as shown on the left right display.

FIG. 19C illustrates a zoomed in image of a virtual object of a solid mass from which a second user is focusing on the inner portions of the solid mass.

1908 illustrates the solid mass, which is being worked on and processed by the second user, which contains a first inner feature 109, a second inner feature 1910 and a third inner feature 1911. Note that the second user has performed edge enhancement of the segmented features, which is illustrates by the black lines surrounding each inner feature and the black line surrounding the mass. Also, note that the transparency adjustment is performed. These processing steps are described in U.S. Pat. No. 10,586,400, PROCESSING 3D MEDICAL IMAGES TO ENHANCE VISUALIZATION, which is incorporated by reference in its entirety.

FIG. 19D illustrates what a second user would see through a HDU. 1912 illustrates the HDU with a left eye display and a right eye display. 1913 illustrates the solid mass, which is being worked on by the second user, as shown on the left eye display. Note that the solid mass 1908 is of greatest interest to the second user and is actively being worked on by the second user. However, the second user is also interested in what the solid mass looks like with the processing that is undergone by the first user and the third user. 1914 illustrates the solid mass as processed the first user as shown on the left eye display. 1915 illustrates the solid mass as processed the third user as shown on the left eye display. 1916 illustrates the solid mass as processed by the second user as shown on the right eye display. 1917 illustrates the solid mass as processed by the first user as shown on the right eye display. 1918 illustrates the solid mass as processed by the third user as shown on the left right display.

FIG. 19E illustrates a zoomed in image of a virtual object of a solid mass from which a third user is focusing on a section of the solid mass. 1919 illustrates the solid mass, which is being worked on and processed by the second user, the top of which has been resected. This technique is taught in U.S. patent Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

FIG. 19F illustrates what a third user would see through a HDU. 1920 illustrates the HDU with a left eye display and a right eye display. 1921 illustrates the solid mass, which is being worked on by the third user, as shown on the left eye display. Note that the solid mass 1921 is of greatest interest to the second user and is actively being worked on by the second user. However, the second user is also interested in what the solid mass looks like with the processing that is undergone by the first user and the third user. 1922 illustrates the solid mass as processed by the second user as shown on the left eye display. 1923 illustrates the solid mass as processed by the first user as shown on the left eye display. 1924 illustrates the solid mass as processed by the third user as shown on the right eye display. 1925 illustrates the solid mass as processed by the second user as shown on the right eye display. 1925 illustrates the solid mass as processed by the first user as shown on the left right display. To even further teach this innovative concept, consider a 5 cm radius mass (approximately sphere shaped) comprising of 1 mm isotropic voxels (1 mm×1 mm×1 mm). This small mass has nearly 520,000 voxels. The inner imaging features and the surface are of specific interest because it is those imaging features that drive diagnosis. Each user is trying to analyze the complex mass independently, but also wants to see what the other users are doing. This collaborative approach is useful for improving diagnosis. Furthermore, this type of process can be utilized in an educational fashion, such as in games wherein speed to detect and classify a relevant finding drives score.

FIG. 20A illustrates a first user at a first time point. 2000 illustrates the first user wearing a HDU. 2001 illustrates the first user's chair. 2002 illustrates the first user's table. 2003 illustrates a virtual object at a first position located at 1.0 meters away from the HDU, which appears over the seated desk. Note that in this patent, the goal is for each user to see the same or similar virtual objects from the same or similar vantage points.

FIG. 20B illustrates a second user at a first time point. 2004 illustrates the second user wearing a HDU who is standing. 2005 illustrates the second user's standing desk. 2006 illustrates a virtual object at a second position located at 1.0 meters away from the HDU, which appears over the seated desk. Note that in this patent, the goal is for each user to see the same virtual objects from the same vantage points. Since the users are in geographically separated regions, each user would have a physical coordinate system that is based on objects in the room.

FIG. 20C illustrates a first user at a second time point. 2000 illustrates the first user wearing a HDU. 2001 illustrates the first user's chair. 2002 illustrates the first user's table. 2007 illustrates a virtual object at a second position located at 0.5 meters away from the HDU, which appears over the seated desk. Note that the scenario was the first user dominant scenario and the first user brought the object inwards deliberately at his/her own will.

FIG. 20D illustrates a second user at a second time point. 2004 illustrates the second user wearing a HDU who is standing. 2005 illustrates the second user's standing desk. 2008 illustrates a virtual object at a second position located at 0.5 meters away from the HDU, which appears over the seated desk. Note that in this patent, the goal is for each user to see the same virtual objects from the same vantage points. Since the users are in geographically separated regions, each user would have a physical coordinate system that is based on objects in the room. The object has been moved by the first user and this can be visualized by a second geographically separated user.

What is claimed is:

1. A method comprising:
    performing rendering of a virtual object, for a first user wearing a first head display unit (HDU), based on the first user's viewing parameters;
    displaying said rendered virtual object based on said first user's viewing parameters on said first HDU to said first user,
    using a predetermined criterion wherein said predetermined criterion comprises at least one of the group of:
        a predetermined viewing angle of said virtual object wherein said predetermined viewing angle is applied to said first user's viewing parameters; and
        a predetermined viewing distance of said virtual object wherein said predetermined viewing distance is applied to said first user's viewing parameters;
    monitoring for presence of said predetermined criterion wherein said predetermined criterion is applied to the first user's viewing parameters; and
    performing rendering of said virtual object, for a second user wearing a second HDU displaying said virtual object, comprising:
        during a time epoch when the predetermined criterion of the first user's viewing parameters is not present,
            performing rendering of said virtual object, for the second user, based on the second user's viewing parameters wherein said second user's viewing parameters of said virtual object are different from said first user's viewing parameters of said virtual object; and
            displaying said rendered virtual object based on said second user's viewing parameters on said second HDU to said second user; and
        during a time epoch when the predetermined criterion of the first user's viewing parameters is present,
            performing rendering of said virtual object, for the second user, based on at least one of the first user's viewing parameters of said virtual object; and
            displaying said rendered virtual object based on said first user's viewing parameters on said second HDU to said second user.

2. The method of claim 1 further comprising wherein the first user's viewing parameter comprises a visual marker.

3. The method of claim 1 further comprising wherein the first user's viewing parameter comprises a manipulated visual appearance of said virtual object.

4. The method of claim 1 further comprising wherein the first user's viewing parameter comprises an image processing status of said virtual object.

5. The method of claim 1 further comprising wherein the predetermined criterion is based on a distance of movement by said first user of at least one of the group of:
the first user's viewpoint;
a geo-registered tool; and
a digital object.

6. The method of claim 1 further comprising wherein the predetermined criterion is based on an extent of rotation by said first user of at least one of the group of:
an orientation of the first user's viewing angle;
an orientation of a geo-registered tool; and
an orientation of a digital object.

7. The method of claim 1 further comprising wherein the predetermined criterion is based on a rate of movement of at least one of the group of:
the first user's viewpoint;
a geo-registered tool; and
a digital object.

8. The method of claim 1 further comprising wherein the predetermined criterion is based on a rate of rotation of at least one of the group of:
an orientation of the first user's viewing angle;
an orientation of a geo-registered tool; and
an orientation of a digital object.

9. The method of claim 1 further comprising wherein the predetermined criterion is based on image manipulation of said virtual object wherein image manipulation of said virtual object comprises at least one of the group of:
filtering portions of said virtual object;
adjusting the virtual object's brightness;
adjusting the virtual object's contrast; and
applying visual enhancement features to said virtual object.

10. The method of claim 1 further comprising wherein the first user causes the first user's virtual object to be moved relative to the first user's HDU which causes the second user's virtual object to be moved relative to the second user's HDU.

11. The method of claim 10 further comprising applying a time delay from a first time point wherein at said first time point the first user's virtual object is moved relative to the first user's HDU to a second time point wherein at said second time point the second user's virtual object is moved relative to the second user's HDU.

12. The method of claim 11 further comprising utilizing a smoothing algorithm for a movement path of the second user's virtual object.

13. The method of claim 1 further comprising:
monitoring for presence of a second predetermined criterion of the second user; and
perform rendering of said virtual object, for the first user, comprising:
during a time epoch when the second predetermined criterion of the second user is not present, performing rendering of said virtual object, for the first user, based on the first user's set of viewing parameters; and
during a time epoch when the second predetermined criterion of the second user is present, performing rendering of said virtual object, for the first user, based on at least one of the second user's first set of viewing parameters.

14. The method of claim 1 further comprising:
utilizing an eye tracking system for the first user to determine the first user's fixation location on the first user's virtual object; and
presenting a digital object on the second user's virtual object at a location on the second user's virtual object corresponding to the first user's fixation location on the first user's virtual object.

15. The method of claim 1 further comprising wherein the first user performs a deformation to the first user's virtual object and wherein the second user can visualize the deformation to the second user's virtual object.

16. The method of claim 1 further comprising wherein the first user's virtual object is displayed with a first visual representation adjustment logic and wherein the second user's virtual object is displayed with a second visual representation adjustment logic wherein said first visual representation adjustment logic is different from said second visual representation adjustment logic.

17. The method of claim 1 further comprising wherein the first user uses a virtual tool to modify the first user's virtual object and wherein the second user's virtual object is modified.

18. The method of claim 1 further comprising wherein the first user uses a geo-registered tool to modify the first user's virtual object and wherein the second user's virtual object is modified.

19. A non-transitory computer-readable storage device comprising:
instructions which, when executed by a computer, cause the computer to carry out the steps of:
performing rendering of a virtual object, for a first user wearing a first head display unit (HDU), based on the first user's viewing parameters;
displaying said rendered virtual object based on said first user's viewing parameters on said first HDU to said first user,
using a predetermined criterion wherein said predetermined criterion comprises at least one of the group of:
a predetermined viewing angle of said virtual object wherein said predetermined viewing angle is applied to said first user's viewing parameters; and
a predetermined viewing distance of said virtual object wherein said predetermined viewing distance is applied to said first user's viewing parameters;
monitoring for presence of said predetermined criterion wherein said predetermined criterion is applied to the first user's viewing parameters; and
performing rendering of said virtual object, for a second user wearing a second HDU displaying said virtual object, comprising:
during a time epoch when the predetermined criterion of the first user's viewing parameters is not present,
performing rendering of said virtual object, for the second user, based on the second user's viewing parameters wherein said second user's viewing parameters of said virtual object are different from said first user's viewing parameters of said virtual object; and
displaying said rendered virtual object based on said second user's viewing parameters on said second HDU to said second user; and
during a time epoch when the predetermined criterion of the first user's viewing parameters is present, performing rendering of said virtual object, for the second user, based on at least one of the first user's viewing parameter of said virtual object; and displaying said rendered virtual object based on said first user's viewing parameters on said second HDU to said second user.

20. An apparatus comprising:

an input-output (IO) device; and an image processor in communication with the TO device, the image processors comprising a program stored on computer-readable non-transitory media, the program comprising:

instructions that perform rendering of a virtual object, for a first user wearing a first head display unit (HDU), based on the first user's viewing parameters;

instructions that display said rendered virtual object based on said first user's viewing parameters on said first HDU to said first user instructions that use a predetermined criterion wherein said predetermined criterion comprises at least one of the group of:
 a predetermined viewing angle of said virtual object wherein said predetermined viewing angle is applied to said first user's viewing parameters; and
 a predetermined viewing distance of said virtual object wherein said predetermined viewing distance is applied to said user's viewing parameters;

instructions that monitor for presence of said predetermined criterion wherein said predetermined criterion is applied to the first user's viewing parameters; and instructions that perform rendering of said virtual object, for a second user wearing a second HDU displaying said virtual object, comprising:

during a time epoch when the predetermined criterion of the first user's viewing parameters is not present,
 performing rendering of said virtual object, for the second user, based on the second user's viewing parameters wherein said second user's viewing parameters of said virtual object are different from said first user's viewing parameters of said virtual object; and
 displaying said rendered virtual object based on said second user's viewing parameters on said second HDU to said second user; and during a time epoch when the predetermined criterion of the first user's viewing parameters is present,
 performing rendering of said virtual object, for the second user, based on at least one of the first user's viewing parameters of said virtual object; and displaying said rendered virtual object based on said first user's viewing parameters on said second HDU to said second user.

* * * * *